United States Patent
Anderson et al.

(12) 
(10) Patent No.: US 6,653,151 B2
(45) Date of Patent: Nov. 25, 2003

(54) DRY DEPOSITION OF MATERIALS FOR MICROARRAYS USING MATRIX DISPLACEMENT

(75) Inventors: Norman G. Anderson, Rockville, MD (US); N. Leigh Anderson, Washington, DC (US); James A. Braatz, Beltsville, MD (US)

(73) Assignee: Large Scale Proteomics Corporation, Germantown, MD (US)

( * ) Notice: Subject to any disclaimer, the term of this patent is extended or adjusted under 35 U.S.C. 154(b) by 63 days.

(21) Appl. No.: 09/772,974

(22) Filed: Jan. 31, 2001

(65) Prior Publication Data

US 2001/0012537 A1 Aug. 9, 2001

Related U.S. Application Data

(63) Continuation-in-part of application No. 09/628,339, filed on Jul. 28, 2000, which is a continuation-in-part of application No. 09/482,460, filed on Jan. 13, 2000.
(60) Provisional application No. 60/146,653, filed on Jul. 30, 1999.

(51) Int. Cl.$^7$ ............................................. G01N 33/543
(52) U.S. Cl. ........................ 436/518; 435/7.1; 436/524; 427/2.11
(58) Field of Search ...................... 435/6, 7.1; 436/501, 436/518, 524; 427/163.2, 256, 287, 429, 275, 399, 2.11

(56) References Cited

U.S. PATENT DOCUMENTS

| | | | |
|---|---|---|---|
| 4,238,757 A | 12/1980 | Schenck | |
| 4,264,408 A | * 4/1981 | Benham et al. | ............. 156/629 |
| 4,459,360 A | 7/1984 | Marinkovich | |
| 4,623,355 A | 11/1986 | Sawruk | |
| 4,708,931 A | 11/1987 | Christian | |

(List continued on next page.)

FOREIGN PATENT DOCUMENTS

| | | |
|---|---|---|
| DE | 19823454 | 11/1999 |
| EP | 274824 | 7/1988 |
| EP | 708483 | 4/1996 |
| EP | 717113 | 6/1996 |
| EP | 721016 | 7/1996 |

(List continued on next page.)

OTHER PUBLICATIONS

Arnold MA., " Enzyme–based fiber optic sensor." *Anal Chem* (1985) 57:565–566.

(List continued on next page.)

*Primary Examiner*—Long V. Le
*Assistant Examiner*—Gary Counts
(74) *Attorney, Agent, or Firm*—Roylance, Abrams, Berdo & Goodman, L.L.P.

(57) ABSTRACT

A method is disclosed which relates to the placement of binding partners on microarrays, where such binding partners contain proteins, nucleic acids, biological cells and other bio-reactive components. The present invention discloses uses and methods for manufacture of microarrays constructed in part by sectioning bundles of tubules or rods containing matrix immobilized bio-reactive molecules to produce large numbers of sample chips. The chips so produced are processed by deposition to microarrays. The deposited chips can then be manipulated to partition the immobilizing matrix away from the bio-reactive molecules contained in the matrix and to place said partitioned molecules onto various surfaces for subsequent analysis, to include binding assays, hybridization reactions, diagnostic methods and a variety of cell interaction-determining methodologies.

8 Claims, 2 Drawing Sheets

U.S. PATENT DOCUMENTS

| | | | |
|---|---|---|---|
| 4,896,363 | A | 1/1990 | Taylor et al. |
| 4,981,653 | A | 1/1991 | Marino |
| 5,186,824 | A | 2/1993 | Anderson |
| 5,252,743 | A | 10/1993 | Barrett et al. |
| 5,264,565 | A | 11/1993 | Barrett et al. |
| 5,273,656 | A | 12/1993 | Anderson et al. |
| 5,302,707 | A | 4/1994 | Campbell et al. |
| 5,324,633 | A | 6/1994 | Fodor et al. |
| 5,338,665 | A | 8/1994 | Schatz et al. |
| 5,362,899 | A | 11/1994 | Campbell |
| 5,420,328 | A | 5/1995 | Campbell |
| 5,424,186 | A | 6/1995 | Fodor et al. |
| 5,432,018 | A | 7/1995 | Barrett et al. |
| 5,451,683 | A | 9/1995 | Barrett et al. |
| 5,482,867 | A | 1/1996 | Barrett et al. |
| 5,491,074 | A | 2/1996 | Aldwin et al. |
| 5,498,530 | A | 3/1996 | Schatz et al. |
| 5,512,131 | A * | 4/1996 | Kumar et al. ............ 156/655.1 |
| 5,527,681 | A | 6/1996 | Holmes |
| 5,540,828 | A | 7/1996 | Yacynych |
| 5,545,531 | A | 8/1996 | Rava et al. |
| 5,571,639 | A | 11/1996 | Hubbell et al. |
| 5,578,832 | A | 11/1996 | Trulson et al. |
| 5,585,275 | A | 12/1996 | Hudson et al. |
| 5,585,646 | A | 12/1996 | Kossovsky et al. |
| 5,593,839 | A | 1/1997 | Hubbell et al. |
| 5,607,691 | A | 3/1997 | Hale et al. |
| 5,622,944 | A | 4/1997 | Hale et al. |
| 5,624,711 | A | 4/1997 | Fujimoto et al. |
| 5,635,597 | A | 6/1997 | Barrett et al. |
| 5,648,458 | A | 7/1997 | Cwirla et al. |
| 5,654,276 | A | 8/1997 | Barrett et al. |
| 5,655,560 | A | 8/1997 | Kedar et al. |
| 5,668,110 | A | 9/1997 | Barrett et al. |
| 5,677,195 | A | 10/1997 | Winkler et al. |
| 5,690,894 | A | 11/1997 | Pinkel et al. |
| 5,710,000 | A | 1/1998 | Sapolsky et al. |
| 5,723,584 | A | 3/1998 | Schatz |
| 5,728,802 | A | 3/1998 | Barrett et al. |
| 5,733,729 | A | 3/1998 | Lipshutz et al. |
| 5,739,386 | A | 4/1998 | Holmes |
| 5,744,305 | A | 4/1998 | Fodor et al. |
| 5,751,629 | A | 5/1998 | Nova et al. |
| 5,759,779 | A | 6/1998 | Dehlinger |
| 5,763,175 | A | 6/1998 | Brenner |
| 5,767,234 | A | 6/1998 | Yanofsky et al. |
| 5,770,456 | A | 6/1998 | Holmes |
| 5,786,331 | A | 7/1998 | Barrett et al. |
| 5,811,238 | A | 9/1998 | Stemmer et al. |
| 5,817,751 | A | 10/1998 | Szardenings et al. |
| 5,834,758 | A | 11/1998 | Trulson et al. |
| 5,843,655 | A | 12/1998 | McGall |
| 5,856,101 | A | 1/1999 | Hubbell et al. |
| 5,874,214 | A | 2/1999 | Nova et al. |
| 5,874,219 | A | 2/1999 | Rava et al. |
| 5,880,096 | A | 3/1999 | Barrett et al. |
| 5,885,837 | A | 3/1999 | Winkler et al. |
| 5,917,016 | A | 6/1999 | Holmes |
| 5,922,545 | A | 7/1999 | Dower et al. |
| 5,925,562 | A | 7/1999 | Nova et al. |
| 5,932,433 | A | 8/1999 | Schatz |
| 5,932,579 | A | 8/1999 | Campbell et al. |
| 5,945,334 | A | 8/1999 | Besemer et al. |
| 5,945,522 | A | 8/1999 | Cohen et al. |
| 5,961,923 | A | 10/1999 | Nova et al. |
| 5,968,740 | A | 10/1999 | Fodor et al. |
| 5,974,164 | A | 10/1999 | Chee |
| 5,990,112 | A | 11/1999 | Campbell et al. |
| 5,993,627 | A | 11/1999 | Anderson et al. |
| 6,013,440 | A | 1/2000 | Lipshutz et al. |
| 6,020,026 | A * | 2/2000 | Birch et al. ................ 427/287 |
| 6,022,963 | A | 2/2000 | McGall et al. |
| 6,025,129 | A | 2/2000 | Nova et al. |
| 6,025,601 | A | 2/2000 | Trulson et al. |
| 6,027,880 | A | 2/2000 | Cronin et al. |
| 6,027,894 | A | 2/2000 | Sapolsky et al. |
| 6,060,288 | A | 5/2000 | Adams et al. |
| 6,140,135 | A | 10/2000 | Landegren et al. |
| 6,187,537 | B1 * | 2/2001 | Zinn et al. .................... 435/6 |
| 6,210,910 | B1 | 4/2001 | Walt et al. |

FOREIGN PATENT DOCUMENTS

| | | |
|---|---|---|
| EP | 728520 | 8/1996 |
| EP | 785280 | 7/1997 |
| EP | 799897 | 10/1997 |
| EP | 812922 | 12/1997 |
| EP | 913507 | 1/1998 |
| EP | 848067 | 6/1998 |
| EP | 926260 | 6/1999 |
| EP | 953210 | 8/1999 |
| EP | 950720 | 10/1999 |
| EP | 955085 | 11/1999 |
| EP | 955382 | 11/1999 |
| EP | 961174 | 12/1999 |
| EP | 967217 | 12/1999 |
| GB | 2262163 | 6/1993 |
| JP | 6301565 | 1/1988 |
| JP | 63010560 | 1/1988 |
| JP | 63010561 | 1/1988 |
| JP | 63010562 | 1/1988 |
| JP | 63010564 | 1/1988 |
| JP | 63010565 | 1/1988 |
| JP | 63172454 | 7/1988 |
| JP | 1213662 | 8/1989 |
| JP | 5109722 | 4/1993 |
| JP | 6085240 | 3/1994 |
| JP | 6256753 | 9/1994 |
| WO | 8302669 | 8/1983 |
| WO | 8703965 | 7/1987 |
| WO | 880875 | 11/1988 |
| WO | 9015070 | 12/1990 |
| WO | 9107087 | 5/1991 |
| WO | 9117271 | 11/1991 |
| WO | 9119818 | 12/1991 |
| WO | 9210092 | 6/1992 |
| WO | 9210587 | 6/1992 |
| WO | 9210588 | 6/1992 |
| WO | 9306121 | 4/1993 |
| WO | 9308278 | 4/1993 |
| WO | 9309668 | 5/1993 |
| WO | 9310161 | 5/1993 |
| WO | 9311565 | 6/1993 |
| WO | 9322680 | 11/1993 |
| WO | 9322684 | 11/1993 |
| WO | 9325197 | 12/1993 |
| WO | 9406808 | 3/1994 |
| WO | 9410128 | 5/1994 |
| WO | 9417792 | 8/1994 |
| WO | 9418345 | 8/1994 |
| WO | 9425043 | 11/1994 |
| WO | 9428173 | 12/1994 |
| WO | 9500530 | 1/1995 |
| WO | 9504069 | 2/1995 |
| WO | 9511922 | 5/1995 |
| WO | 9511988 | 5/1995 |
| WO | 9511995 | 5/1995 |
| WO | 9512608 | 5/1995 |
| WO | 9518971 | 7/1995 |
| WO | 9520973 | 8/1995 |
| WO | 9522058 | 8/1995 |
| WO | 9522625 | 8/1995 |

| | | |
|---|---|---|
| WO | 9525177 | 9/1995 |
| WO | 9531210 | 11/1995 |
| WO | 9533846 | 12/1995 |
| WO | 9535278 | 12/1995 |
| WO | 9535505 | 12/1995 |
| WO | 9600148 | 1/1996 |
| WO | 9600378 | 1/1996 |
| WO | 9600391 | 1/1996 |
| WO | 9605214 | 2/1996 |
| WO | 9616333 | 5/1996 |
| WO | 728520 | 8/1996 |
| WO | 9623813 | 8/1996 |
| WO | 9629088 | 9/1996 |
| WO | 9633736 | 10/1996 |
| WO | 9636732 | 11/1996 |
| WO | 9639165 | 12/1996 |
| WO | 9640204 | 12/1996 |
| WO | 9640738 | 12/1996 |
| WO | 9640749 | 12/1996 |
| WO | 9640987 | 12/1996 |
| WO | 9702357 | 1/1997 |
| WO | 9710365 | 3/1997 |
| WO | 9720078 | 6/1997 |
| WO | 9727317 | 7/1997 |
| WO | 9729212 | 8/1997 |
| WO | 9739151 | 10/1997 |
| WO | 9741093 | 11/1997 |
| WO | 9743450 | 11/1997 |
| WO | 9743611 | 11/1997 |
| WO | 9749845 | 12/1997 |
| WO | 9812354 | 3/1998 |
| WO | 9812559 | 3/1998 |
| WO | 9916103 | 4/1998 |
| WO | 9818967 | 5/1998 |
| WO | 9820967 | 5/1998 |
| WO | 9824796 | 6/1998 |
| WO | 9827430 | 6/1998 |
| WO | 9829535 | 7/1998 |
| WO | 9830883 | 7/1998 |
| WO | 9838846 | 9/1998 |
| WO | 9839348 | 9/1998 |
| WO | 9841657 | 9/1998 |
| WO | 9844100 | 10/1998 |
| WO | 9846551 | 10/1998 |
| WO | 9853841 | 12/1998 |
| WO | 9856954 | 12/1998 |
| WO | 9858529 | 12/1998 |
| WO | 9859072 | 12/1998 |
| WO | 9859360 | 12/1998 |
| WO | 9859361 | 12/1998 |
| WO | 9859362 | 12/1998 |
| WO | 9902682 | 1/1999 |
| WO | 9904440 | 1/1999 |
| WO | 9905323 | 2/1999 |
| WO | 9905324 | 2/1999 |
| WO | 9905574 | 2/1999 |
| WO | 9905591 | 2/1999 |
| WO | 9906833 | 2/1999 |
| WO | 9909218 | 2/1999 |
| WO | 9918434 | 4/1999 |
| WO | 9927105 | 6/1999 |
| WO | 9928475 | 6/1999 |
| WO | 9932662 | 7/1999 |
| WO | 9935256 | 7/1999 |
| WO | 9937659 | 7/1999 |
| WO | 9939004 | 8/1999 |
| WO | 9940105 | 8/1999 |
| WO | 9945021 | 9/1999 |
| WO | 9945357 | 9/1999 |
| WO | 9950456 | 10/1999 |
| WO | 9951733 | 10/1999 |
| WO | 9951778 | 10/1999 |
| WO | 9954509 | 10/1999 |
| WO | 9954718 | 10/1999 |
| WO | 9963113 | 12/1999 |
| WO | 9964626 | 12/1999 |
| WO | 9965945 | 12/1999 |
| WO | 0000808 | 1/2000 |
| WO | 0004372 | 1/2000 |
| WO | 0006771 | 2/2000 |
| WO | 0011223 | 3/2000 |
| WO | 0040942 | 7/2000 |
| WO | 0065098 | 11/2000 |

OTHER PUBLICATIONS

Bronk et al., " Fabrication of patterned sensor arrays with arylazides on a polymer–coated imaging optical fiber bundle." *Anal Chem* (1994) 66:3519–3520.

Gautler et al., "Fiber optic biosensor based on luminescence and immobilized enzymes: Microdetermination of sorbitol, ethanol and oxaloacetate." *J Biolum Chemilum* (1990) 5:57–63.

Walt et al., "Self regenerating fiber opic sensors." In *Direct Monitoring of Antigen–Antibody Interactions by Special Interferometry*. ACS Symposium Series (1995) 586:186–196.

Ferguson et al., "A fiber–optic DNA biosensor microarray for the analysis of gene expression." *Nat Biotech* (1996) 14:1681–1684.

* cited by examiner

DRY DEPOSITION OF MATERIALS FOR MICROARRAYS USING MATRIX DISPLACEMENT

CROSS REFERENCE TO RELATED APPLICATIONS

This application is a continuation-in-part of patent application Ser. No. 09/628,339 filed Jul. 28, 2000, which is a continuation-in-part of patent application Ser. No. 09/482,460 filed Jan. 13, 2000 which is a continuation-in-part of Provisional Patent Application Ser. No. 60/146,653 filed Jul. 30, 1999, the contents of which are incorporated herein in entirety.

FIELD OF THE INVENTION

The present invention relates to placement of many compounds on a surface in a predefined pattern. Moreover, the present invention discloses uses and methods for manufacture of microarrays having these compounds bound in the predefined pattern to the surface.

BACKGROUND OF THE INVENTION

Synthesis and analysis of large numbers of bound oligonucleotides or peptides are generally known in the art. For example, the Selectide bead approach uses vast quantities of spherical cross-linked polymer beads (Millipore or Cambridge Research Laboratories polyacrylamide beads or Rapp Tentagel polystyrene) divided into 20 equal piles, each of which then has a different L-amino acid coupled to all the beads in the pile. The bead piles are then combined and thoroughly mixed. The resulting single pile is again divided into 20 different piles, each of which is reacted with a different one of the 20 different L-amino acids. This Divide, Couple and Recombine process (DCR) is repeated through six reactions to produce hexapeptides bound to the beads. The beads are then screened against a "target" molecule that is labeled with a conjugated enzyme, such as horseradish peroxidase. The target "sticks" to active hexapeptide(s). The bead is rendered visible by adding a substrate for the enzyme that converts it to a colored dye, which is precipitated within the beads, and then the visually identified bead(s) are picked out with tweezers. The peptides on the beads are then analyzed, for example by the Edman sequencing method, and soluble versions produced in a synthesizer. The initial screening (locating the target bead(s)) takes only days, the makeup of each identified hexapeptide is unknown, and the analysis and synthesis for confirmation and further work takes much longer. Such sorting and resorting becomes too burdensome and labor intensive for the preparation of large arrays of peptides. Further, this process can be characterized as not calling for a continuous support, and it is not addressable.

Another approach, using arrays, is the pin dipping method for parallel oligonucleotide synthesis. Geysen, J. Org. Chem. 56, 6659 (1991). In this method, small amounts of solid support are fused to arrays of solenoid controlled polypropylene pins, which are subsequently dipped into trays of the appropriate reagents. The density of arrays, however, is limited, and the dipping procedure employed is cumbersome in practice.

Disclosed at the Southern, Genome Mapping Sequence Conference, May 1991, Cold Spring Harbor, N.Y., is a scheme for oligonucleotide array synthesis in which selected areas on a glass plate are physically masked and the desired chemical reaction is carried out on the unmasked portion of the plate. The problem with this method is that it is necessary to remove the old mask and apply a new one after each interaction. Fodor et al., Science 251, 767 (1991) describes another method for synthesizing very dense 50 micron arrays of peptides (and potentially oligonucleotides) using mask-directed photochemical de-protection and synthetic intermediates. This method is limited by the slow rate of photochemical de-protection and by the susceptibility to side reactions (e.g., thymidine dimer formation) in oligonucleotide synthesis. Khrapko et al., FEBS Letters 256, 118 (1989) suggest simplified synthesis and immobilization of multiple oligonucleotides by direct synthesis on a two-dimensional support, using a printer-like device capable of sampling each of the four nucleotides into given dots on the matrix. For example, the probes are applied to a chip with a pin or a pipette in the pattern of an array and immobilized by any of a variety of techniques such as adsorption or covalent linkage. An example of such DNA arrays is described in Stimpson et al. Proc. Natl. Acad. Sci. USA Vol. 92, pp. 6379–6383, July 1996. Since elements of the array are formed by the application of a DNA solution to the surface of the array the process is relatively slow. The development of VLSIPS.TM. technology has provided methods for making very large arrays of oligonucleotide probes in very small arrays. See U.S. Pat. No. 5,143,854 and PCT patent publication Nos. WO 90/15070 and 92/10092. U.S. patent application Ser. No. 082,937, filed Jun. 25, 1993, describes methods for making arrays of oligonucleotide probes that can be used to provide the complete sequence of a target nucleic acid and to detect the presence of a nucleic acid containing a specific nucleotide sequence. One drawback to this method is that it relies on a new DNA synthesis chemistry as opposed to the standard phosphoramidite chemistry used in commercial DNA synthesizers. The technology feeds off the methods evolved in the electronics industry and therefore has some of the same requirements, vis, accurate positioning to micron scales, clean room requirements and the use of multiple photo-masks to define the array pattern. Although electronic "chips" (for example an Intel Pentium.RTM. microprocessor) are mass-produced economically, they are typically too expensive to be used as a disposable element, as is needed with a DNA chip.

A common limitation to many of these methods is due to depositing liquids on surfaces, i.e., "spreading." For example, spreading occurs on derivatized surfaces, such as those used in DNA immobilization on glass supports, because the solid support surface becomes hydrophilic upon derivatization. As a result, when the DNA (desired to be immobilized upon the solid support) is contacted with the surface of the solid support, it spreads, rather than remaining in a discrete "spot." Spreading is a major constraint on array density (i.e., the number of different spots that can be arranged on a single solid support). Hence, any means to curtail spreading, and so increase array density, is highly desirable.

Additional problems arise with the density of biomolecule spotted on the solid support. Droplets of liquid will form a meniscus, which inherently causes uneven liquid thickness and the edges will dry at a different period of time from the center of the droplet. Thus, the coverage of biomolecule on the surface remaining may be uneven.

Still further when forming a microarray by spotting technology, the total amount of biomolecule deposited on the region of the microarray is limited to the maximum amount soluble in the droplet. For insoluble or low solubility molecules, this becomes a limiting factor.

Unfortunately, all of the array fabrication methods mentioned above also suffer from the same general problem in that each element of each array is a unique synthesis or an application step. This is true even when array elements or entire arrays are simply duplicated or produced "in parallel", or more accurately, concurrently. Since each element is a unique synthesis or application there is a chance for variation between corresponding elements on different arrays or, for that matter, duplicated elements on the same array. Even in a photolithographic process, increasing the number of chips on a wafer (the substrate on which multiple arrays are produced) results in an increase in surface area, which increases demand on the chemicals used in photochemistry (assuming no change in chip size).

What is needed in the art are methods to enhance the amount of material that attaches to a solid support and to increase the reliability and reproducibility with which materials are applied to a solid support. The present invention helps meet that need.

Biochemical molecules on microarrays have been synthesized directly at or on a particular cell on the microarray, or preformed molecules have been attached to particular cells of the microarray by chemical coupling, adsorption or other means. The number of different cells and therefore the number of different biochemical molecules being tested simultaneously on one or more microarrays can range into the thousands. Commercial microarray plate readers typically measure fluorescence in each cell and can provide data on thousands of reactions simultaneously thereby saving time and labor. A representative example of the dozens of patents in this field is U.S. Pat. No. 5,545,531.

Currently two dimensional arrays of macromolecules are made either by depositing small aliquots on flat surfaces under conditions that allow the macromolecules to bind or be bound to the surface, or the macromolecules may be synthesized on the surface using light-activated or other reactions. Previous methods also include using printing techniques to produce such arrays. Some methods for producing arrays have been described in "Gene-Expression Micro-Arrays: A New Tool for Genomics", Shalon, D., in Functional Genomics; Drug Discovery from Gene to Screen, IBC Library Series, Gilbert, S. R. & Savage, L. M., eds., International Business Communications, Inc., Southboro, Mass., 1997, pp 2.3.1.-2.3.8; "DNA Probe Arrays: Accessing Genetic Diversity", Lipshutz, R. J., in Functional Genomics; Drug Discovery from Gene to Screen, IBC Library Series, Gilbert, S. R. & Savage, L. M., eds., International Business Communications, Inc., Southboro, Mass., 1997, pp 2.4.1.-2.4.16; "Applications of High-Throughput Cloning of Secreted Proteins and High-Density Oligonucleotide Arrays to Functional Genomics", Langer-Safer, P. R., in Functional Genomics; Jordan, B. R., "Large-scale expression measurement by hybridization methods: from high-densities to "DNA chips"", J. Biochem. (Tokyo) 124: 251–8, 1998; Hacia, J. G., Brody, L. C. & Collins, F. S., "Applications of DNA chips for genomic analysis", Mol. Psychiatry 3: 483–92, 1998; and Southern, E. M., "DNA chips: Analyzing sequence by hybridization to oligonucleotides on a large scale", Trends in Genetics 12: 110–5, 1996.

Regardless of the technique, each microarray is individually and separately made, typically is used only once and cannot be individually precalibrated and evaluated in advance. Hence, one depends on the reproducibility of the production system to produce error-free arrays. These factors have contributed to the high cost of currently produced biochips or microarrays, and have discouraged application of this technology to routine clinical use.

For scanning arrays, charged coupled device (CCD) cameras are widely used. The cost of these has declined steadily, with suitable cameras and software now widely available. However, in one proposed variation, an array is located at the ends of a bundle of optical fibers with the nucleic acid or antibody/antigen attached to the end of the optical fiber. Detection of fluorescence may then be performed through the optical fiber, see U.S. Pat. No. 5,837,196.

Fiber optical arrays are routinely produced in which glass or plastic fibers are arrayed in parallel in such a manner that all remain parallel, and an optical image may be transmitted through the array. Parallel arrays may also be made of hollow glass fibers, and the array sectioned normal to the axis of the fibers to produce channel plates used to amplify optical images. Such devices are used for night vision and other optical signal amplification equipment. Channel plates have been adapted to the detection of binding reactions (U.S. Pat. No. 5,843,767, not prior art) with the individual holes being filled after sectioning of the channel plate bundle, and discrete and separate proteins or nucleic acids being immobilized in separate groups of holes.

Hollow porous fibers have been widely used for dialysis of biological samples, in kidney dialyzers and for water purification. Methods for aligning them in parallel arrays, for impregnating the volume between them with plastic, and for cutting the ends of such arrays have been described (see, for example, U.S. Pat. No. 4,289,623).

Immobilized enzymes have been prepared in fiber form from an emulsion as disclosed in Italy Pat. No. 836,462. Antibodies and antigens have been incorporated into solid phase fibers as disclosed in U.S. Pat. No. 4,031,201. A large number of other different immobilization techniques have been used and are well known in the fields of solid phase immunoassays, nucleic acid hybridization assays and immobilized enzymes, see, for example, Hermanson, Greg, T. Bioconjugate Techniques. Academic Press, New York. 1995, 785 pp; Hermanson, G. T., Mallia, A. K. & Smith, P. K. Immobilized Affinity Ligand Techniques. Academic Press, New York, 1992, 454 pp; and Avidin-Biotin Chemistry: A Handbook. D. Savage, G. Mattson, S. Desai, G. Nielander, S. Morgansen & E. Conklin, Pierce Chemical Company, Rockford Ill., 1992, 467 pp.

Scanners and CCD cameras have been described to detect and quantitate changes in fluorescence or absorbance and are suitable for existing biochips. These, together with suitable software, are commercially available.

Currently available biochips include only one class of immobilized reactant, and perform only one class of reactions. For many types of clinical and other analyses, there is a need for chips that can incorporate reactants immobilized in different ways in one chip.

SUMMARY OF THE INVENTION

The present invention relates to a method for forming a predefined pattern of compounds or biological materials on a solid support where the compounds or materials are present in a matrix forming a solid. Individual compounds or biological materials are held in different portions of the matrix or separate matrixes bundled together prior to contacting the solid support. Actual deposition of the compounds or biological materials occurs when the matrix is removed/degraded/melted/partitioned from the compounds or biological materials or otherwise reversibly attached so that the compounds or biological materials are free to bind to the solid support.

More particularly, the present invention relates to a method for producing a microarray comprising immobilized chemicals or components at predefinable addresses by dry dispensing such materials onto solid surfaces. More specifically, the invention relates to a method of dry dispensing bio-reactive components to a surface such that the components are uniformly distributed within a defined area at a high density on the surface. Specifically, the method comprises placing a solid containing compounds or components in a solidifying matrix onto a surface, degrading the matrix and retaining the entrapped compounds or components on the surface at the predefined locations by adherence thereto. Moreover, retaining the reactive compounds comprises displacing the matrix, where the displacing step uniformly deposits the entrapped bio-reactive samples on the solid surface. Such displacement can comprise the use of abutting the matrix on at least one porous membrane comprising the solid surface.

In a further aspect, the bio-reactive samples are embedded or immobilized in a meltable/removable/degradable/dissolvable or otherwise reversible matrix, which comprise rods or tubules. Each rod or tubule may contain different or identical entrapped material samples. Further, the rods or tubules can be used for checking that all elements of the bundle maintain a constant arrangement or pattern throughout the length of the bundle after immobilization/embedding and for sectioning the bundle to produce large numbers of identical chips for forming the desired pattern on the solid surface. Moreover, the resulting arrays are used for performing a variety of different quantitative biochemical analyses based on enzymatic activities, immunochemical activities, nucleic acid hybridization and small and large molecule and complex binding. These analyses are performed under conditions yielding to detection by fluorescence, optical absorbance or chemiluminescence signals, for acquiring images of these signals that are electronically processed and compared to produce clinically and experimentally useful data. The components can include, but are not limited to biological macromolecules, complexes, organelles, biological cells (i.e., prokaryotic and eukaryotic) and viruses. For example, the macromolecules can include, but are not limited to proteins, carbohydrates, nucleic acids and lipids.

In a further aspect of the invention, the solid containing coating agent and matrix is formed from slices obtained from a solid fiber, filament or tube.

In one aspect, the invention relates to long fibers, filaments or tubes comprising a meltable/removable/degradable/dissolvable matrix that contain or have the compounds or components embedded/immobilized therein, and methods for their manufacture. More specifically, microarrays are constructed in part by sectioning bundles of tubules or rods containing matrix immobilized molecules to produce large numbers of chips. The chips so produced are further processed by deposition to form microarrays. The deposited chips are subsequently manipulated to partition the immobilizing matrix away from the desired molecules or components, and to place said partitioned molecules onto the surface of the microarray.

In another aspect, the matrix can be made from various materials including, but not limited to super-cooled liquids, crystals, crystal polymers, non-crystal polymers, gels, waxes, emulsions, highly thickened or very viscous liquids, colloid suspensions, plastic and cleavable linkages to a solid. In some situations, the matrix may be as simple as ice.

The present invention improves the well known spotting technique for making microarrays by completely avoiding any possibility of droplets smearing, spilling, mixing with its neighbor, etc. by "spotting" with a solid rather than a liquid. The present invention also increases the amount per unit area of protein/DNA/viruses/biological cells/various organic compounds coated on the slide (or other solid phase). The present invention also allows one to place more addressable locations/cells per square centimeter of solid phase (e.g., the slide etc.) because a solid rather than a liquid is depositing the material.

This invention further relates to a method for the large scale production of identical flat two-dimensional arrays of immobilized nucleic acid-based bio-reactive samples for use in nucleic acid sequencing, in the analysis of complex mixtures of ribonucleic acids (RNAs) and deoxyribonucleic acids (DNAs), and in the detection and quantitation of other samples including proteins, polysaccharides, organic polymers and low molecular mass analytes with other arrays, by sectioning long bundles of meltable/removable/degradable/dissolvable matrix comprising fibers or tubes. Large scale production of other identical flat surfaces having a pattern of compounds or materials may be prepared by the same methods.

In another aspect of the present invention, one may perform quality control assays on each fiber after manufacture, so that only fully functional fibers are included in a fiber bundle and fully functional sliced chips are used for depositing onto a solid surface.

In a further related aspect the invention relates to the development of sets of tests on different chips done in optionally branching sequence, which reduces the cost, delay, and inconvenience of diagnosing human diseases, while providing complex data ordinarily obtained by time-consuming sequential batteries of conventional tests.

In still another aspect, the invention relates to the fabrication of identical arrays that are sufficiently inexpensive to allow several identical arrays to be mounted on the same slide or test strip, and cross-compared for quality control purposes.

In yet another aspect, the present invention relates to multi-welled plates and methods for their manufacture where the wells are coated to contain a reagent where the reagent is added in a solidifying matrix which is subsequently degraded to deposit the reagent on the inside of the well.

In yet a further aspect, the invention relates to increasing the dynamic range of multiple-parallel assays by providing means for making serial measurements of fluorescence or absorbance over time, and for determining the rate of change of fluorescence or absorbance in each element of the array over time. By preparing a microarray with the same immobilized compound or component in different concentrations, a more quantative result may be obtained. As the present invention permits a greater range of amounts to be deposited on a unit of surface area, a more sensitive and wider sensitivity range may be achieved.

It is an additional aspect of this invention to produce biochips which are inexpensive and sufficiently standardized to allow more than one to be used for each analysis, and for controls and standards to be routinely run simultaneously in parallel. For added quality assurance, sections from different portions of the bundle or different ends may be used. One way of sectioning from different portions of the bundle is to cut or bend the bundle in the middle and align the two halves to form a single larger bundle thereby producing a section where each fiber is represented twice.

In a further aspect, this invention relates to the production of chips in which the array elements or cells may differ from one another in the composition of the tubes, supporting medium, immobilization surface, immobilization matrix, or the class of agent of interest may be different in different cells.

It is another aspect of the invention to have differential deposition by altering the conditions and materials. Different matrixes may be used for immobilizing different chemicals or components as needed and have different dissolving rates and degradation conditions.

In an additional aspect, the invention relates to the production of microarrays in which different types of reactions may be carried out at the surface of each cell of the array on to which the chemicals or materials have been placed, with the reactions including immunological, enzymatic, hybridization or other binding reactions.

A further aspect of this invention relates to the production of subbundles of fibers or tubules adhering together to form one-dimensional ribbon-like arrays, which may be separately stored. These may be subject to quality control analysis before being assembled into two-dimensional arrays. Different one dimensional and partial two dimensional arrays may be used to assemble different arrays. Thus, providing the option of producing custom-made arrays to meet specific research and clinical requirements.

In a still further aspect, the invention relates to preparing libraries of compounds with each fiber containing one of the compounds. Libraries of cells, microorganisms, and subcellular structures may also be prepared and used. The array may be used to simultaneously screen all of the compounds for a particular chemical or biological activity or conversely to screen a candidate compound against a number of biological materials.

DETAILED DESCRIPTION OF THE INVENTION

Figure 1:
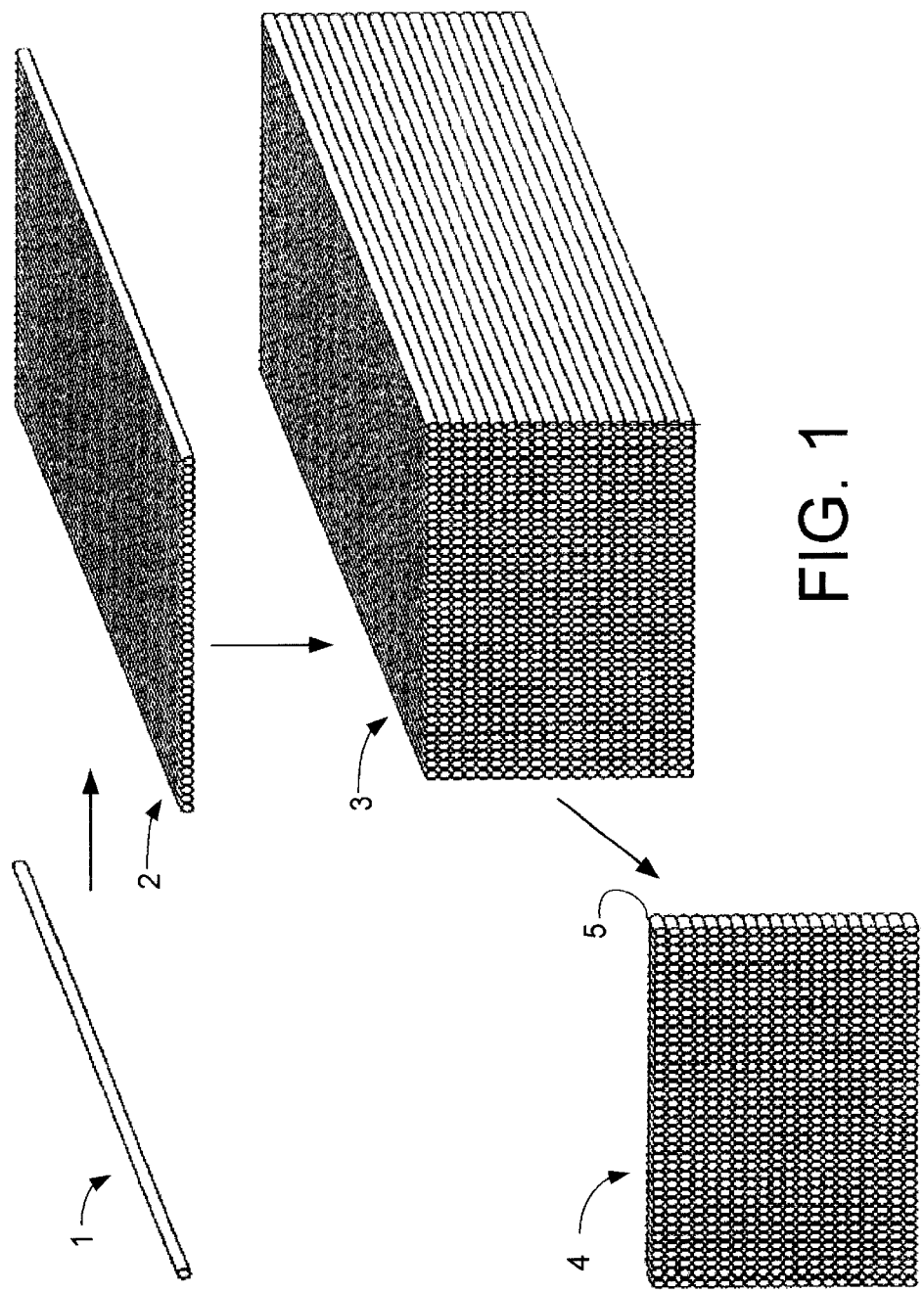
FIG. 1 depicts the components and steps involved in making a sliced section.
Figure 2A:
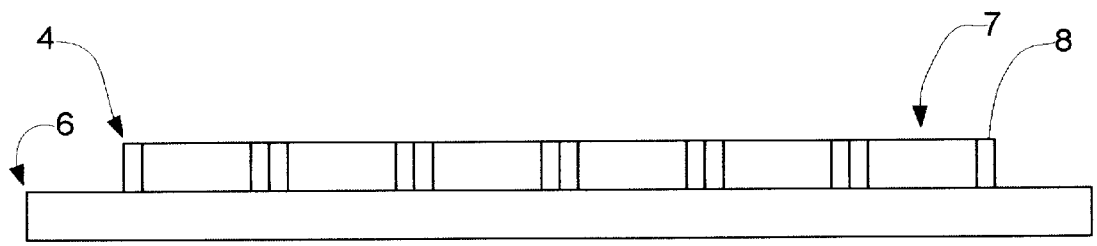
FIGS. 2A, 2B and 2C are cross-sectional views of a sliced section on a solid surface and the steps involved in preparation of the final microarray.
Figure 2B:
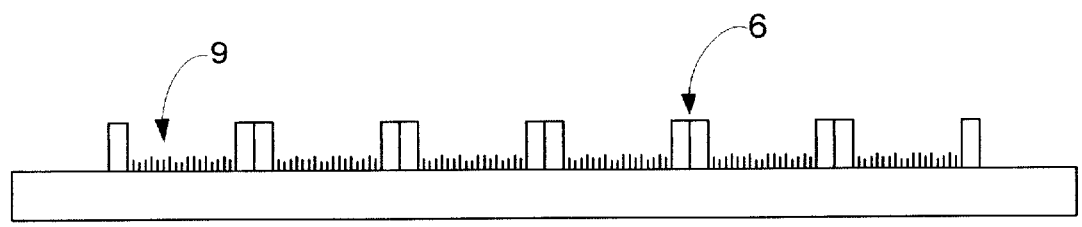
Figure 2C:
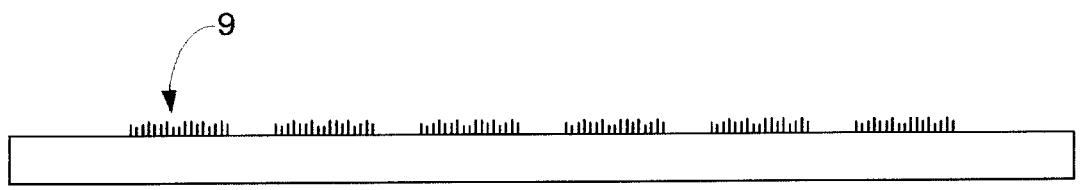

The terms "binding component," "molecule of interest," "agent of interest," "ligand" or "receptor" may be any of a large number of different chemical molecules, complexes, biological cells, fractions thereof or aggregates, and the terms are used interchangeably to describe various compounds and components or material. Each binding component is immobilized at a cell, site or element of the array and binds to an analyte being detected. Therefore, the location of an element or cell containing a particular binding component determines what analyte will be bound. Proteins, polypeptides, peptides, nucleic acids (oligonucleotides, peptide nucleic acids and polynucleotides), antibodies, ligands, polysaccharides, microorganisms such as bacteria, fungi and viruses, receptors, antibiotics, test compounds (particularly those produced by combinatorial chemistry), or plant and animal cells and organelles or fractions of each may each be a binding component if immobilized in the chip and subsequently deposited on the solid surface. Each, in turn, may also be considered as analytes if they bind to a binding component immobilized on a chip, where the immobilized component is subsequently deposited on the solid surface.

When a molecule of interest has a high molecular weight, it is frequently referred to as a "macromolecule". In terms of some biopolymers, the high molecular weight refers to greater than 100 amino acids, nucleotides or sugar molecules long.

The term "bind" includes any physical attachment or close association, which may be permanent or temporary. Generally, an interaction of hydrogen bonding, hydrophobic forces, van der Waals forces, affinity, covalent and ionic bonding etc., facilitates physical attachment between the molecule of interest and the analyte being measuring. The "binding" interaction may be brief as in the situation where binding causes a chemical reaction to occur. This is typical when the binding component is an enzyme and the analyte is a substrate for the enzyme. Reactions resulting from contact between the binding agent and the analyte are also within the definition of binding for the purposes of the present invention.

The term "cells", "sites", "addresses" or "elements" in this application refers to a unit component of an array identified by a unique address and these generally differ from other cells, sites or elements by their content as well as location. Biological cells are referred to by their type, e.g. microorganisms, animal and plant cells.

The term "fibers" includes both filaments and hollow capillaries. Filaments or rods may be solid strands of monolithic, porous, or composite forms, or aggregate forms. Pluralities, typically a large number, of fibers are bound adjacent to each other in ribbons or bundles to form a "fiber bundle." A fiber bundle may constitute a portion of the actual bundle being used such as ribbon. The cross-section of the fibers may be of any shape, such as round, triangular, square, rectangular or polygonal.

The term "particle" includes a large number of insoluble materials of any configuration, including spherical, thread-like, brush-like and many irregular shapes. Particles are frequently porous with regular or random channels inside them. Examples include silica, cellulose, Sepharose beads, polystyrene (solid, porous and derivitized) beads, controlled-pore glass, gel beads, sols, biological cells, subcellular particles, microorganisms (protozoans, bacteria, yeast, viruses, etc.) micelles, liposomes, cyclodextrins, two phase systems (e.g. agarose beads in wax) etc. and other structures which entrap or encapsulate a material. Particularly preferred are recombinant hosts and viruses that express the protein of interest. Even certain high molecular weight materials, such as, polymers and complexes, may serve as immobilizing structures that would constitute a "particle".

The term "sintering" refers to the adhesion of the surfaces of the fibers without actually melting the whole fiber. Sintering may be chemical or thermal and may even involve a self-adhesive component that may be activate-able.

The term "dry dispensing" refers to depositing binding components in a solidifying matrix to a solid surface without applying using a liquid vehicle. Further, the matrix is removed in such a way as to retain the comprising bioreactive sample on the solid surface. A dry dispensed product may contain water or other liquid, as long as it retains a solid shape during handling.

In a preferred embodiment, the solid phase surface is selected from the group consisting of glass, ceramics, Teflon coated materials; organic polymers and biopolymers. In a related aspect, binding molecules such as, but not limited to for example, protein G, protein A, streptavidin, biotin, receptors, ligands, lectins, and nucleic acids, are prebound to a solid phase surface. This binding can be done by any means known in the art such as, but not limited to, the methods of Burzio et al. (U.S. Pat. No. 5,817,470), Löfas et al. (U.S. Pat. No. 5,716,854), Thust et al. (U.S. Pat. No. 5,955,335) and Hiriade et al. (U.S. Pat. No. 5,736,099). These prebound materials may act to immobilize agents of interest after the matrix is removed.

The term "uniformly distributed" refers to a substantially equal concentration of bio-reactive components within a defined analysis field (area).

The term "porous membrane" refers to a surface that will allow for the partitioning of a matrix (e.g., once a change in physical state of the matrix has occurred, solid to fluid), away from the immobilized components in said matrix. In a preferred embodiment, the porous membrane abuts or is the solid surface, wherein such abutting allows for complete removal of the matrix from the solid surface by, for example, passage through the membrane. In a related aspect, the sample could be partitioned by electrophoresing the sample out of the matrix onto a porous membrane (e.g., Western transfer).

"Meltable matrix," "removable matrix," "degradable matrix" "reversible matrix" and "dissolvable matrix" are interchangeable terms referring to any immobilizing medium that can: 1) in the solid state comprise a uniform dispersion of agent of interest as a suspension without substantially affecting the functional properties of the agent 2) be converted to a state, including, but not limited to a fluid and/or gas, that allows for facile partitioning away of said medium from said sample 3) be cleaved from a solid phase such as the inside walls of the fiber tube 4) be chemically or electrically altered to render unable to continue to immobilize the agent of interest, all without adversely affecting the functional properties of the agent.

An example of a meltable matrix is a low melting point waxes such as castor wax, steryl alcohol, many polymers, etc. An example a removable matrix is a silica or other particulate thickened medium such as clays. An example of a degradable matrix is protease digestible gelatin or amylase digestible starch or a pH, chemical or temperature sensitive matrix. An example of a reversible matrix is alginate with calcium or sodium ions determined by the presence of a chelating agent and the like. An example of a soluble matrix is a sugar or soap with water as solvent or fatty acids with organic solvents. The list of possibilities is very long.

The terms "arrays" and "microarrays" are used somewhat interchangeably differing only in their general size and number of addressable locations or cells. The present invention involves the same methods for making and using either. Each array typically contains many cells (typically 100–1,000,000+) wherein each cell is at a known location and contains a specific component of interest. Each array therefore contains numerous different components of interest.

The present invention makes microarrays or "chips" by sectioning bundles of small plastic rods, fibers, tubes or tubules containing immobilized binding component, including biological molecules and entities such as nucleic acid fragments, antigens, antibodies, proteins, peptides, carbohydrates, ligands, receptors, drug targets, biological cells or their subfractions (e.g., ground-up cells, solvent extract, etc.), infectious agents or subfractions of them, drugs, toxic agents, or natural products, etc. Embedding media may be, in the present invention, solidified in small tubes, or may be cast into rods or sheets.

The tubes may be of material such as glass, metal, ceramic or plastic. The immobilized binding components, e.g. nucleic acids, proteins, cells, etc., may be coated on the inside or outside of the microtubes, contained in a gel in the microtubes, or attached to or embedded in small particles or beads which fill the tubes. The particles or beads may be a component of a gelling material or can be separate components such as latex beads made of a variety of synthetic plastics (polystyrene, etc.). When the individual fibers are solid rods or filaments, the agent of interest is incorporated into the medium before the filament is cast, extruded or pulled through a die. Each section cut constitutes a microarray for use in various binding assays.

A key aspect of this invention, which provides an economic advantage, is that the fibers or tubules are prepared using only methods providing a functionality stable to long term storage. Unlike other methods involving protein containing liquids that must be prepared fresh each time, immobilized proteins in relatively dry form remain stable for great lengths of time, often without refrigeration.

The preparation of each component of a future microarray separately in/on a fiber permits one to assay for and evaluate the functionality or reactivity of each component before being incorporated in an array. Both the spotting technique and the in-situ synthesis technique do not permit testing before completion. Furthermore, quality control checks can only sample a small portion of such microarrays, which is unlike the present invention where each fiber may be tested.

In the prior art spotting technique, a 1 mm diameter liquid droplet is generally at most 0.5 mm when on a solid surface. By contrast, a 1 mm diameter solid cylinder may be 3 or more mm tall, potentially depositing six (6) times more protein/DNA etc. on the same area of surface given the same solubility of protein etc. Hence, the same unit area of solid surface may have a considerably larger range of protein density. The same applies different amounts of fluid and different surface areas and for any other agents of interest and the solid cylinder may be of almost any height.

Furthermore, solids may be placed on smaller areas a surface than liquids, which allows one to place more addressable locations/cell per square centimeter of solid phase (the slide etc.). Microarrays are known in the art and are commercially available from a number of sources. Microarrays have been used for a number of analytical purposes, typically in the biological sciences. An array is essentially a two-dimensional sheet where different portions or cells of the sheet have different biomolecule elements, such as, nucleic acids or peptides, bound thereto. Microarrays are similar in principle to other solid phase arrays except that assays involving such microarrays are performed on a smaller scale, allowing many assays to be performed in parallel.

Various aspects of the invention are illustrated in FIGS. 1 and 2A, 2B and 2C. General principles for forming a sliced chip are illustrated in FIG. 1 where a rod or tube 1 incorporates an agent of interest in a solid matrix. The rods or tubes may be bonded into a flat parallel ribbon 2, and multiple flat ribbons are then bonded into the multiple-parallel bundle 3. Alternatively, the bundle 3 may be constructed in one step from a series of rods 1. The end of bundle 3 is cut or sectioned to yield the sliced section 4 that contains one small piece 5 of each rod or tube in the entire bundle. By making a long bundle 3, and cutting very thin sections 4, a very large number of identical chips or slices are formed. In one embodiment, if bundle 3 is a meter long, and the sections are 10 microns thick, 100,000 identical chips may be produced.

In FIG. 2, the thin section 4 is mounted on a solid surface 6, which is to become the microarray. Remnants of the hollow fiber tube 8 separate remnants of individual fibers 7. After application of the matrix removing step, the agents of interest adhere to and form a layer 9 on the surface. Optional final removal of the remnants of individual fibers 7 yields a solid surface with a layer 9 in a predefined pattern of various agents of interest.

For the present purposes, in the case of hollow glass fibers, such as those in channel plates, the hollow fibers may be filled with matrix and binding partner, and the entire bundle sawed into sectioned chips for use in preparing microarrays.

The rods or tubules comprising the sectioned bundle may be characterized separately. The different types fall into at least five classes, with subdivisions of each.

In a first class, solid rods or filaments are formed with the immobilized binding component being part of the composition of the rod or filament. Alternatively, a solid fiber may be impregnated by electrophoresing the agent of interest through the matrix of the solid fiber.

In a second class, fibers are not homogeneous and the solidifying matrix may also contain solid structural elements such as filaments, branched elements, particles, etc., to further strengthen the gel or and may also provide attachment sites for the agent of interest that can also be readily partitioned away from free agents. Polystyrene latex or other plastic particles to which proteins or nucleic acids are attached are particularly preferred. Conditions can be arranged such that the supporting plastic is eroded to a depth of a few microns to reveal active subparticle surfaces, and do not dissolve the supporting plastic latex beads. For example, proteins derivatized with fluorinated groups attach strongly to Teflon®, microparticles. Such derivatized Teflon® particles in, other suitable embedding medium, can be partially exposed at the plastic surface by a dilute solvent, composed. Alternatively, these particles may be embedded in a porous matrix. The beads to which agents of interest are attached may be porous gel beads used in chromatography such as Sephadex, Biogels and others, or solid beads such as are used in chromatography. A variety of methods for derivitizing these and for attaching proteins, nucleic acids and polysaccharides and small molecules thereto have been developed and are well known to those skilled in the arts. Thus, the added components serve to strengthen the gel, and may provide attachment sites for inclusions including dendrimer branched polynucleic acids, branched or crosslinked polymeric materials, metal or glass fibers. Threads, yarn-like and brush-like configurations of structural elements may be cast into the length of the fiber giving it strength and allowing the fiber to be more easily handled or dried. The structural elements may serve as the immobilizing component in the fiber for a desired binding component. The structural elements may later adhere to the solid surface as a method for adhering the binding partner.

A third class of fibers includes extruded or cast matrix, which includes a second phase. This second phase may be in the form of, for example, hydrocarbon, aqueous or fluorocarbon microdroplets, particles of sugars, wax, inorganic particles such as calcium carbonate particles, which can be dissolved in dilute acid or other suitable materials. Brief exposure of the surface of a chip to a solvent will dissolve some of these inclusions, increasing the surface area of the support material containing the agents of interest and allowing them to adhere to the solid surface directly or indirectly via the porous solid. These solid matrixes can also be prepared which incorporate structural elements as in the second class of fiber.

In a fourth class, fibers are comprised of hollow impermeable tubules typically formed from plastics including, but not limited to polyethylene, polypropylene, Teflon®, or polyvinyl chloride, and are completely filled with a matrix to which agents of interest are attached or suspended. Alternatively, the agents of interest may be reversibly or cleavably bound to the inner surface of these hollow tubes. The external surfaces of the tubes may be chemically or physically modified to accept adhesives used to bind the bundled tubes together. The tubes may be filled before or after bundling.

The inside surfaces of the small tube described may be modified chemically to allow reversible attachment of nucleic acids, proteins or other molecules either directly or through linkers known per se. The molecules attach, thus increasing the number of reactive sites inside the tube. Since DNA and RNA are conventionally synthesized on small polystyrene beads, the most direct approach to a nucleic acid array is to synthesize oligonucleotides on small polystyrene beads, with different batches of beads having different sequences attached, and to then fill small polyethylene, polypropylene, polystyrene or other plastic, metal or ceramic tubes with the beads, packing them down to completely fill them. The beads may be kept in place by carefully heating them to sinter or residual latex is added to the tubes and dried in place with air pumped through the tube.

Tubes or fibers may include tubules with permeable walls. Methods and procedures for producing hollow selectively-permeable fibers for use in kidney dialysis machines and for molecular weight fractionation have been extensively developed (U.S. Pat. No. 4,289,623, U.S. Pat. No. 3,976,576) and are in wide current use. Procedures for embedding such fibers in solid sectionable plastics have also been developed and are routinely used to attach the fibers to tubing at the dialyzer ends.

Permeable hollow fibers may be used in the present invention in two ways. In the first, the fibers are filled with agent and liquefied matrix. By carefully splaying out the fibers going into the cast portion, each tube can be selectively filled as previously described. This technique offers the advantage of producing small arrays quickly, and of developing new assays without having to go through all of the steps required to produce separate hollow fibers, fill them with reactants, arrange them in arrays, and infiltrate them with the supporting plastic.

Another method of use involves filling the hollow fibers before they are embedded in plastic. Techniques have been developed for controlling the wall permeability of permeable tubes. This allows the influx and outfluxes of monomers and gelling agents during gelation to be controlled, and for dialyzable agents to be removed after gelling.

One such example is the use of hollow fibers porous to calcium ions where the agent of interest is mixed in an sodium alginate solution and pumped through the hollow fiber. When submerged in calcium chloride, calcium alginate gels form thereby entrapping the agent of interest. These gels are reversible in a chelating solution such as EDTA.

Permeable supporting tubing also allows the gel inside a tube to be infiltrated with substances that render the reactants more stable, increase the physical strength of the gel, and facilitate sectioning. For example, sugars such as lactose, trehalose, glycerol, fructose and other polyhydric alcohols may be introduced to stabilize proteins, and to add solids to the gels to assist in sectioning. These additives may be removed from the exposed surface of the chip during use to make buried reactive groups available. Additives diffusing into the gels may also be used to increase the strength and volume of a gel after it has been dried. Permeable tubing also enhances water removal during drying if so desired.

In preferred embodiment, an element of a microarray is formed by mixing a biological reactive molecule with a matrix which is subsequently removed from the element of the microarray, allowing the biological target molecule to then react with a component of a surface with which it is in contact, to provide a stable linkage between biological target molecule and the surface. In a related aspect, a protein can be used for this purpose that has a recognition site for another molecule, such as biotin, which can be bound by strepavidin. This biotinylated-protein can be mixed with a reversible gelling system, such as but not limited to, agarose. Cylindrical tubular elements can be formed in which the elements are comprised of the reversible gel containing a biological target molecule. Once formed into an array, thin sections can be prepared and mounted on a surface that contains immobilized recognition factors, such as in this case strepavidin. The gel can then be dissolved or removed by any means to expose the biological target molecule that is then free to diffuse and react with the immobilized recognition factor. This has the advantage of eliminating the support polymer as a barrier to reactants and can serve to increase the processing time for analyte detection. The recognition system can be comprised of many types of interactions, such as, but not limited to, antigen-antibody, lectin-carbohydrate, and in general, any of the well known ligand receptor systems. Reversible gels can be comprised of, but not limited to heat reversible agar or agarose systems, reversible polyacrylamides, metal dependent alginate systems, redox dependent disulfide containing polymeric systems (e.g., polymers formed by oxidation of sulfhydryl groups to disulfides that can be reduced back to free sulfhydryl groups). In addition, the support matrix may be one that can be degraded by any means to liberate the entrapped biological target molecule. The degradation process can consist of, but would not be limited to acid or base hydrolysis, enzymatic hydrolysis, photodegradation, temperature change such as with thermal responsive polymers which are solid or liquid, depending on the temperature, and other processes known in the art.

In a related aspect, the gel can be dissolved and removed by filtration through the porous support. In such an embodiment, the biological target molecule would then be retained by the receptor attached to the porous support.

Also, when a particle containing the ligand or receptor is embedded in a fiber, the embedding medium is soluble, reversible, degradable or meltable to be removable after the microarray is formed. By removing the embedding medium, the ligand or receptor is available to bind to the solid support. This variation is particularly preferred when the particle is actually microfibers or microbrushes of microfilaments having the immobilized ligands or receptors thereon are sedimentable to the solid surface.

Once the tubes are filled with their respective matrixes and reagents, the outside of the tubes are cleaned, may be treated with reagents to increase the adherence of the infiltrating supporting plastic, and then bundled to produce the product for sectioning.

The method of embedding is one that preserves the desired characteristic or characteristics of the binding component in a cell. Thus, if antibodies were immobilized in a cell and it is the antigen-binding specificity of the antibody that is desired, the immobilization method will be one which retains the antigen-binding ability of the antibodies. The method and means of attaching the fibers to form the array are also ones that retain the antigen-binding ability of the antibodies.

Similarly, if the cells contain candidate molecules for binding to a hormone receptor, the immobilizing and attaching method and means are those that retain the configuration of the candidate molecules that allows recognition and binding by the hormone receptor.

In addition, many protein or carbohydrate antigens may be detected using immunological reagents. Detection is generally by incorporation of a fluorescent dye into the analyte or into the second layer of a sandwich assay, or by coupling an enzyme to an analyte or a second or third layer of a sandwich assay that produces an insoluble dye, which may be fluorescent.

Some solid phase surfaces may be used directly to immobilize reactants; others must be modified to allow such additions. Antibodies will adhere to clean polystyrene surfaces, as will many other proteins (Van Oss, C. J., & Singer, J. M. The binding of immune globulins and other proteins by polystyrene latex particles. J. Reticuloendothelial Society 3: 29040, 1966.) Polystryene, in the form of microtiter plates, has been modified to bind nucleic acids, proteins, and polysaccharides using techniques that are well known. Teflon® surfaces will tenaciously bind proteins or other macromolecules that have been suitably fluorinated (U.S. Pat. No. 5,270,193), and will bind fluorinated surfactants, which may render the surface hydrophilic, or positively or negatively charged. Glass, including controlled pore glass, may be modified to allow covalent attachment of antibodies, antigens or nucleic acids. Plastic surfaces may be modified non-specifically using corona plasma discharge or electron beam radiation and may then be coated with a variety of coatings or adhesives to which macromolecules may be attached. More specific covalent attachment of proteins, nucleic acids or carbohydrates may be achieved by a variety of modifications which attach reactive groups to polystyrene or acrylic surfaces, which groups, with or without extending linkers, will then couple under mild conditions to the biopolymers.

A variety of chromatographic media has also been adapted to support immobilized bioreactants. These include gels, generally composed of acrylamide, agarose, Sepharose, which may be chemically cross-linked. Chief among natural products useful as an immobilization support is cellulose that is readily available in powdered form. These supports may be chemically modified to allow covalent bioreactant attachment, or may be purchased in modified form ready for attachment.

Long DNA or RNA molecules may be immobilized by being polymerized in a gel and are retained purely by physical entanglement. An example of this is the retention of DNA in agar or acrylamide gels. In addition, proteins or nucleic acids may be covalently linked to long polymer chains so that, when embedded in a gel, they are prevented from prematurely diffusing out, but are still available for reaction with soluble reactants. Examples of this include the attachment of proteins or nucleic acids to polyethylene glycol (so-called PEGylation), or other polymer chains.

In addition to methods by which a receptor or molecule of interest is immobilized and used to bind an analyte, general methods exist for immobilizing members of a class of reactants. For example, protein A or protein G may be immobilized and used to subsequently bind specific immunoglobulins which in turn will bind specific analytes. A more general approach is built around the strong and specific reaction between other ligands and receptors such as avidin and biotin. Avidin may be immobilized on a solid support or attached to a gel and used to bind antibodies or other reactants to which biotin has been covalently linked. This allows the production of surfaces to which a very wide variety of reactants can be readily and quickly attached (see Savage et al., Avidin-Biotin Chemistry: A Handbook. Pierce Chemical Company, 1992).

A wide variety of methods has been developed to detect reactions between immobilized molecules of interest and soluble reactants. These differ chiefly in the mechanism employed to produce a signal, and in the number of different reagents that must be sandwiched together directly or indirectly to produce that signal. These include fluorescence (including delayed fluorescence) with the fluorescent tag covalently attached to the analyte, fluorescence involving soluble dyes, which bind to an analyte, and similar dyes whose fluorescence greatly increases after binding an analyte. The latter are chiefly used to detect nucleic acids. In more complex systems, including so-called sandwich assays, the result is the immobilization in the detection complex of an enzyme that, in combination with a soluble substrate, produces a preferably insoluble dye that may be fluorescent. Alternatively, the detection complex attached to the bound analyte may include a dendritic molecule, including branching DNA, to which is attached many fluorescent dye molecules.

Methods for making dental floss having attached short transverse fibers to give a brush-like configuration have been described, and these may be modified to allow attachment of reactants. Patterns encoding identifying information on strands or fibers may be employed in the form of small linearly arranged dots. In the development of multifiber endoscopy arrays, methods for checking the array have been developed in which a light beam or raster image is introduced at one end of the fiber bundle in such a manner that the light sequentially illuminates each fiber. The pattern of emitted light exiting the other end is then determined. If they are identical, no fiber is out of place.

The art of detecting bubbles or voids in liquid filled tubing is well known, and may depend on differences in refraction, or light absorption or fluorescence as measured along individual tubes. The art of using centrifugal force to fill short lengths of small tubing with viscous media is evident to those trained in the arts.

Microtomes for sectioning tissue blocks which may contain samples ranging from soft tissues to bone, often in blocks of embedding material (e.g. wax), are commercially available, as are a variety of techniques and arrangements for attaching sections to glass or plastic slides, for treating them automatically to remove some or all of the embedding media, and for systematically exposing the slides to a series of reagents.

Microtomes and other sectioning or cutting instruments capable of cutting assembled bundles of tubes into thin sections, and of maintaining their orientation after sectioning are known. In general, blade cutting is preferred to sawing to reduce contamination of binding components between cells of the microarray. Further, means of distributing and aligning separate chips may also be used.

The sections (as microarray chips) may be attached directly to adhesive surfaces on flexible films or on solid surfaces, such as glass slides. It is preferable that the solid phase be coated or derivitized to include moieties for specifically or non-specifically binding the reagents freed by removing the matrix. It is also feasible to attach sections (the word "section" is used here in place of "chip") at intervals along a film strip, with others interleaved between them. Thus, a set of about a dozen or more sections that are different may be placed in repeating order along the film, and the film then cut up to give one set. For sequencing studies, one DNA insert may be amplified, labeled, and its hybridization to a large set of sections examined.

By using a non-deformable bundle of fibers, one can cut or saw the bundle transversely thereby forming a large number of identical plates that are perfectly realignable. This permits highly consistent and reproducible arrays. By using an easily detectable different material for one or more fibers, as a means for registering the microarray alignment, realignment is even easier.

Most immunochemical or competition assays depend on a signal produced by a reagent other than the analyte. However, methods for fluorescently labeling all proteins containing aliphatic amino groups in a complex mixture have been developed which are reproducible and quantitative. Of these CyDyes supplied by Amersham Life Sciences, and particularly, Cy2, Cy3 and Cy5 have proven most useful. When the components of such labeled mixtures are reacted with an array of immobilized antibodies, each specific antibody binds to one of the fluorescently labeled analytes, and the presence of each of the specifically bound labeled analyte can be detected by fluorescence. This method can be further improved by exposing the bound antibody array to a solution containing known subsaturating quantities of each analyte protein in a non-fluorescent form, washing the array, and exposing it to a test mixture of labeled proteins, thus producing a multiple competition assay.

Any of the conventional binding assay formats and detection formats involving an immobilized binding partner, known per se in hundreds of patents, may be used with the microarray systems of the present invention. Briefly, the microarray may have either plural ligands or plural receptors and the analyte may be either plural ligands or plural receptors. Competing elements that bind to either the analytes or the microarray cells may be added. The sample may be labeled and/or the competing element may be labeled and/or the microarray cell may be labeled. The labels may be interacting with each other to make a detectable signal or product or to quench a signal or product. The number of different combinations is in the dozens and any of them may be used in the present invention as well as different combinations for different cells of the microarray assay.

It is well known that several different clinical tests are often required to define a particular disease. These are often done serially, with one test or member of a battery of tests suggesting another, which in turn suggests a third test or group of tests, some of which are rarely done in local laboratories. There is therefore a need for inexpensive chips for the performance of a series of branching batteries of tests all at one time, using methods that produce accurate numerical results in a machine readable form, which are stable over time, and which are read by devices that can be compact and inexpensive relative to currently clinical analytical systems.

Many biochemical analyses require that the analytical procedure have wide dynamic range. Thus, enzyme and immunochemical assays are often done by determining the course of a reaction over a period of time, or by doing the analyses on a series of dilutions. Such analyses may be done by "reading" the microarrays at intervals during exposure to an analyte mixture of a developing reagent. This allows one to use an excess of labeled reagent that will initially detect high abundance ligands followed by overexposure of these microarray addresses and the beginning of detection of low abundance ligands. This system is most useful when the detection system involves an enzyme or slow reaction that becomes more intense over time such as the silver staining procedure used in photography and protein detection. In addition, parallel analyses using standards and blanks (controls) are required and are universally included. Large numbers of standardized inexpensive biochips will be required to meet these needs. These biochips may incorporate reactants of different classes that can, for example, detect and measure antigens, drugs, nucleic acids or other analytes.

Arrays have numerous uses other than determining bioactive properties. Chemical interactions and reactions may be tested as well such as an array of different reactive chemicals being tested against a test substance or material to determine corrosion, electrochemical reaction or other interaction. This is particularly advantageous in the chemical formulations of plural substances such as in cosmetics, paints, lubricants, etc. Alternatively, one may assay for desirable interactions between the analyte and all of the molecules of interest in the array.

The resulting surface may also be used for affinity chromatography, affinity separations, protein—protein binding to form protein complexes and the measurement for all of these.

The present invention also may also coat the surface with materials other than organic chemicals and biological materials. Different metals, anticorrosive coatings, decorative or instructional coatings, coatings for surface plasmon resonance (see U.S. Pat. No. 5,955,729), coatings for SELDI (see U.S. Pat. No. 6,020,208), combinatorial libraries of chemicals, and even coatings for depositing photoresists, electrically conductive coatings etc. such as are used in electronic integrated circuits.

A general problem with use of gels for the immobilization of reactants has been that reactants, which may attach to gel-immobilized agents of interest, require considerable time to diffuse into and out of the gel. By using removable immobilizing medium and partitioning of medium away from agents of interest with subsequent deposit of the latter to a solid phase, this problem is circumvented.

Using a porous membrane also has certain advantages in washing the microarray to achieve lower backgrounds. If porous particles or threadlike components are embedded within the fiber, sectioning through the porous particle or threadlike component may make it more porous and allow greater surface area contact to both reagents and washing. Etching of an embedding medium or capillary also increases porosity and exposure to the immobilized molecules of interest.

If a porous particle is sectioned, preferably twice, larger channels allowing passage that is more fluid may be present. Fibers with these sectioned particles may be mounted over permeable membrane supports or over holes in a solid base support. The result allows fluid to pass through the cells of the microarray.

By using the present invention, one avoids the difficulties of individually spotting each cell on a solid phase or forming a compound at each cell. The former technique is limited by the spill, maximum practical concentration and ability to quantitatively measure small quantities of liquid. The later technique is limited by the types of different compounds that can be synthesized on the solid phase. Both prior art techniques are expensive and require elaborate automated equipment or tedious labor as each array is individually produced. By contrast, the present invention is technically simple and quick where the "batch" is in the thousands to millions of microarrays. The only individual effort required for each microarray are the steps of cutting and placement of sliced sections.

Microarrays prepared from sets of stored reagents or by the synthesis of different reactive sequences or compounds on the base chip present difficult problems in quality control. With large arrays, each reagent in its final form cannot be separately assayed in solid form before being used, nor can the correctness of the in-situ synthesized sequences be assured until after a set of arrays have been manufactured. If errors or substandard components are discovered in a batch of arrays, all must be discarded. These problems limit the use of "biochips" in routine clinical studies. It is well known that immobilized proteins and nucleic acids are more stable in a dry state than they are in solution.

The agent of interest in the present invention may comprise a very broad range of chemicals, complexes, biological cells or fractions thereof. Nucleic acids, many proteins, proteins which have been modified or are coated with detergents such as sodium dodecyl sulfate are soluble in organic solvents and a wide range of organic compounds and thus can be incorporated into polymerizing mixtures such as those used to produce plastics. Hence, it is technically feasible to produce long fibers of acrylic or other plastics each containing a different agent of interest using currently available extrusion technology for practice in the present invention.

Large numbers of different and potentially new active compounds may be simultaneously screened by immobilizing them in fibers, bundling, sectioning and forming a microarray. Peak fractions from separations, such as plant extracts may be simultaneously collected and used to form a microarray. The microarrays may then be used in a large number of assay systems simultaneously, dramatically reducing the time and effort to screen all of the compounds present for whatever activity one chooses.

Particularly preferred are large numbers of proteins or peptides and other combinatorial compounds generated by mass techniques. Different fractions from a separation technique from a natural source provide a resource of many different compounds and biological materials. A number of fractionation procedures are known to separate mixtures of many compounds. Different fractions or specific compositions may be used to form a single fiber. Two dimensional electrophoresis gels from serum and other tissue and natural sources produce thousands of different proteins separated on the gel. Each may be individually removed (e.g. cut, eluted etc.) from the gel and used as the molecule of interest to form a single fiber. In such a method, with different bundles being formed from different samples, protein differences between different samples may be readily compared.

When the immobilized macromolecules are antibodies, the microarray may be used to diagnose a variety of protein-based anomalies. A labeled second antibody to the protein(s) of interest may be used to further highlight the cell. In addition, the array may be used to immobilize infectious agents, which have been either previously stained or which, are stained after immobilization. Thus, microbes from biological samples, e.g. serum or plasma, may be concentrated, stained for a example with a fluorescent nucleic acid stain such as TOTO-1 or YOPRO-1, and then allowed to find their matching antibodies on the array. They may then be detected by scanning for fluorescence and identified by position.

It is equally a part of the present invention to immobilize microorganisms or other molecules of interest and use them to localize antibodies from a patient's sera, and then discover the location of the latter using a fluorescent anti-human antibody, thus diagnosing a disease which elicited antibody production in the first place.

Arrays have been prepared using phage display with inserts from specific genes, using synthetic oligonucleotides, or (to a limited extent) using displayed antigens or antibodies. In the present application, a population of peptide or antibody display phage may be used where each display phage is used to prepare a single fiber. The molecule of interest may be bound to the fiber per se, entrapped inside the matrix, or bound to a solid phase particle or tiny structure which is in or on the fiber. The phage, recombinant bacteria or other complex biostructure may also be fixed and the contained proteins cross-linked using glutaraldehyde or similar fixative, if desirable.

Each fiber may contain a mixture of molecules of interest. For example, during chemical synthesis, a number of isomers are prepared. It is convenient to not separate the isomers before forming a fiber in some circumstances. Likewise, when fractionating a mixture, forming a fiber with a mixture of receptors may be acceptable as total and complete isolation is difficult and time consuming.

Arrays may have an entire set of antigens/antibodies etc. in the various cells along with controls to effectively screen blood samples for common blood borne diseases before donated blood is provided for transfusion. Likewise, certain symptoms have a number of common causes that may be simultaneously screened for using arrays. For example, urinary tract infections are common and may be caused by a large number of different bacteria of varying sensitivity to various antibiotics. The simultaneous testing for a number of different factors would save considerable time and expense.

In the course of using a chip of the instant invention, various known techniques and materials are used to reduce non-specific reaction. Thus, in the case of a protein-based assay, the non-specific sites on the chip contributed by the substance of the fiber or filament, the embedding material and essentially everything aside from the binding component of interest are reacted with a blocking agent, such as albumin or milk, so that the blocking agent will bind to those areas not containing the binding component which could react with a ligand, analyte, reporter molecule or whatever would bind to the binding component, as known in the art.

Arrays may have two or more identical cells made from different fibers but containing identical binding agents. This provides an internal quality assurance check for the array. Additionally, it is preferred for some of the cells to provide different concentrations of the binding component for quantitative measurement of an analyte. These provide internal standards for the microarray for both qualitative detection and quantitative detection. For example, a series of cells may contain different concentrations of an antigens left by their gel fibers. When a sample antibody is contacted with the cells and allowed to incubate, the binding signal in one cell and the absence of binding signal in another cell provide an approximate binding affinity. The same can be done for determining minimal bacteriocidal concentrations when stained with a vital dye such as trypan blue or fluorescein acetate. Since a microarray may contain thousands of separate locations, one can determine the binding affinity of numerous antibodies simultaneously. Quantitative determination of other biological activities with either ligand or receptor immobilized in the gel may be used also.

Essentially the same fiber may be used multiple times in the same microarray. This provides an internal quality control check and improves confidence in the binding assay. This also provides additional quantitative measurements if such an assay is performed to improve precision. Blank fibers, fibers with no molecule of interest bound thereto, provide a good negative control and should be used in every microarray.

Long filaments, capillaries or coaxial two-material filaments are arranged in parallel and then sintered or adhesively bonded to each other to form bundles which are preferably resistant to deformation, and in which each strand or capillary is continuous from one to the other. The positional arrangement of fibers or capillaries should remain the same throughout the bundle. Filaments composed of two different types of material in coaxial formation may be used. The core material is made of a material, which can be dissolved, and the cladding being resistant to the same dissolving conditions. For example, strong alkali is capable of dissolving certain types of glass but not others. The dissolving step may occur before or more preferably after sectioning depending on the materials present.

After the fibers in the bundle are fused or otherwise adhered to each other in a fixed pattern, the bundle is cut transversely or at an angle into many thin disks and portions are optionally dissolved if desired.

Each fiber segment in the sectioned two-dimensional array would contain relatively large numbers of binding components, such as DNA, RNA, or protein molecules.

Because each fiber has the molecule of interest essentially in the same form, as it will appear in the microarray, one can perform a quality control check on the fiber itself rather than using the entire microarray. This is particularly important when the microarray is used for diagnostic purposes. Sampling microarrays from a batch may be a quality control check but it does not actually check the microarrays being sold. By contrast, small slices of the fibers themselves are being used in the present invention. Assaying the fiber itself represents an actual test of every microarray that has a slice of that fiber in a microarray cell.

By contrast, with solid phase in situ synthesis of a molecule of interest directly on each cell of the microarray, none of the actual compositions to be used containing molecules of interest is actually tested for after it is synthesized. Rather spot checking is relied upon for quality assurance. In microarray manufacture by spotting liquid droplets on a solid phase, one may test the liquids as a quality control check. However, these are liquid samples and do not represent the quality of the dry molecules of interest immobilized on a slide. Therefore, the quality control check is not the same as the actual product being sold. Again, one lacks any quality assurance for the actual compositions in the cells of the microarrays being sold.

For quality control in the present invention, the fibers may be individually assayed, assayed in ribbons or small groups or assayed as part of the whole bundle before it is sliced. Furthermore, by testing one final microarray, one has effectively tested all of them, as the composition of the fiber is the same as that portion of the final product.

For clinical tests, regulatory approval of tests and systems and methods for making them is required. When chips are fabricated using photolithography and other technology derived from electronic chip making, the cost of individual chips is quite high, and the possibility of error when chips are individually made is very high. Since chips are individually made and used only once, quality control is difficult and there is no good way of proving that any given chip is satisfactory. The best that can be done is to test a large fraction of a batch at random. With the present invention, a very large number of sections can be made from one composite assembly, and adjacent sections inter-compared as well as those some distance apart. Statistical analyses will be able to predict the rate of errors that may occur. However, of even greater importance is the fact that since the sections can be made in large numbers and quite cheaply, it will be feasible to run duplicate analysis on clinical samples, and to run confirmatory analysis when important diagnostic results are obtained. The present invention therefore makes feasible widespread and routine application of genetic analyses in the practice of medicine.

The key agent of interest component of the fibers is retained by the fiber by being immobilized therein. Immobilization may be accomplished by a number of techniques, known per se, such as entrapment in a matrix and chemically coupled, perhaps through a linking moiety through an amino, hydroxy, sulfhydryl or carboxyl moiety. Chemically attaching the chemical to a monomer or being used as a monomer to be polymerized also effectively incorporates the component. Binding may also be accomplished by a number of affinity techniques such as protein A or protein G for antibody attachment, ligand/receptor pairs such as biotin-avidin, HIV-CD4, sugar-lectin or through a ligand that has a receptor such as digoxigenin-antidigoxigenin. On the other hand, no specific attachment is required for situations where a gel or a non-gel, gelling matrix, such as wax, silicone polymers and silicone emulsions may be used. Liquid wax or a gelling agent is simply mixed with the key component and cooled to form a solid fiber by casting or extruding. Other thickening agents, gums, clays, soaps, fatty alcohols, gels, particulates/crystallites, waxes, emulsions, cooled liquids, etc. are sufficient to form a sectionable semi-solid. For all, the reversible nature of the solid state is important to proper deposition of the agent of interest on the solid phase.

Arrays need not be assembled in a single step. Flat arrays consisting of a set of tubes arranged side-by-side may be prepared first, and the end of the array sectioned and tested. The flat arrays can then be attached together with a suitable adhesive to give a three-dimensional bundle. The use of intermediate flat arrays means that these can be prepared and stored, and custom two-dimensional arrays can be prepared by selecting and attaching together different one-dimensional arrays. This stepwise assembly procedure provides inspection at each step, minimizes losses due to errors or low binding efficiency of one rod or tubule, and provides flexibility to assemble new patterns of reactants.

For general clinical use, it is important to have identifiers on the slide holding the chip, and identifiers may be integral with the chip itself. The bundle as well as individual microarrays may have machine readable indicia such as a barcode printed along one border to provide identification and orientation. In addition, small concentrations of dyes, usually non-fluorescent, may be incorporated into the polymers from which selected tubes are made such that they present a pattern 43 to 44, for example, of one or more numbers, or one or more letters. It is also useful to have a few cells or elements which do incorporate fluorescent dyes or other detectable compound or structure and which serve to calibrate the measurements. It is further feasible to introduce dyes into the contents of selected tubes to additionally identify them. Note that the diagonal line 43–44 further indicates that the horizontal rows of tubes from which the array is assembled, are in the proper order. If tubes in an array are out of alignment giving rise to the loss of one tube or rod in one line, this can be readily observed because the entire pattern will show a misalignment.

The embedding material or adhesive used to hold the tubes in a bundled configuration may be inert and/or opaque, while the tubes and preferably, their contents will conduct light along their length. As a final check on the orientation of array elements, one element at a time at one end of the bundle may be illuminated, and the light detected and related to array position at the other at the other end.

The choice of dissolving or matrix removing liquid depends entirely on the composition of the matrix and the agent of interest to adhere to the solid surface. The selection is at least as broad as that of the matrixes. It is important that this liquid not adversely affect the agent of interest. Such a liquid is not always needed, such as when the matrix is sublimable or heat degradable/meltable.

To prevent the dissolving or matrix removing liquid from removing the material one wishes to deposit on the solid surface, one may leave the inert tubes from the fibers bound to the solid surface at least temporarily to prevent cross contamination of different agents of interest. The liquid may then be evaporated, blotted, aspirated or if the solid surface is a porous membrane, passed through the porous membrane. The same removal techniques may be used for meltable or other removable matrixes that do not require a solvent.

As an alternative method to forming fibers before bundling them, one may first form the fibers by cleaving them from a larger material. A sheet of adsorbent material is impregnated with a single ligand or receptor. This may be done by dissolving the compound in a solution and then impregnating a sheet of adsorbent matrix. A crosslinking agent may be added to attach the receptor to the matrix or other support. Many different sheets are prepared, wherein each sheet contains a different receptor.

The sheets are then stacked together (like a book) with optional adhesive and optionally an inert sheet (not impregnated, preferably black) as a spacer between each sheet of paper. This forms a "book". One then takes the book to a paper cutter or similar sectioning instrument and a very thin strip is cut which resembles the "ribbon" described above. The rest of the process is similar to that above. Multiple strips from different books are stacked to form a bundle that is then cut transversely to form a sectioned slice. An adhesive is preferably added to the ribbons to adhere them. Alternatively, an adhesive may be applied to a solid phase or the end of the bundle and the solid support adhered to the bundle end before sectioning.

Other films, which adsorb protein such as ones having an activated heterobifunctional photoactivatable crosslinking reagents or simple adsorption film such as polyacrylamide or polyurethane may be used. One may use different proteins on different sides of the sheet or film and separate the sheets with an inert sheet to separate cells and signals in the final microarray.

The matrix component may be made of a wide variety of materials as mentioned above. Each material may be a composite of two or more components. The fibers may act as light pipes or total internal reflection fiber optics to transmit positional alignment and information regarding chemical and biological reactions occurring on the surface.

Gelling materials used in the present invention may be selected from a large number of such known materials. Such material must be readily amenable to dissolving, depolymerization, melting or phase (state) transition without substantially effecting immobilized/embedded bio-reactive samples. Polymers such as agarose, gelatin, collagen, xanthene, carrageenan, alginate, or a thermosetting, thermoplastic, chemosetting or UV polymerizing polymer may be used. Non-polymeric gelling materials including thickening waxes and particulates such as clays, silica etc. may be used. Hydrogels are particularly preferred when the agent of interest is to be maintained in an aqueous environment. The polymerizing agent or setting agent may be added after the fiber has been cast by submerging a permeable fiber cast in a solution of the polymerizing agent or passing the agent along the outside of the fiber cast.

Hydrogels have many desirable features such as variable gel porosity, ability to bind proteins during or after polymerization, low non-specific binding, transparency, harmless polymerization byproducts, controllable polymerization open time, usable with a variety of solvents. Reversibility or degradation of the polymer is dependant of the type of bond formed.

These may be further modified by using thickeners, gums, hardening and crosslinking agents, plasticizers and various combinations of gelling materials. In general, the gelling material should be sufficiently inert to not interfere with an interaction between the binding component and an analyte.

In the present invention, an agent of interest may be extracted into solvent, which is miscible in a solidifying matrix. Matrix examples include a thermosetting plastic mixture, or one, which is polymerized chemically or by UV or ionizing radiation. This may be done by coating the agents with detergents or other reagents, which will make them soluble under the conditions chosen. The mixture is then extruded into long fibers or cast into fibers. The fibers may be identified by tags on the end of the fiber or by tags on the rolls carrying the fibers, and/or by incorporating different dyes in them. A barcode may also be printed directly near the end of fibers. Thermoplastic polymers may be used when the embedded product is sufficiently thermostable. Some of the fibers may be differently colored to assist in the localization of specific ligands in the array or to identify the array itself.

The solvent may be miscible in the gelling material or it may be extractable or volatile to render a solid final product. Solid products are preferably filament fibers that are self-supporting.

Different dyes (fluorescent or non-fluorescent) may be incorporated into individual fibers, allowing their location in the two-dimensional array to be confirmed prior to removing the matrix material.

The solid filaments or capillary tubes comprising the fibers may be adhered to each other by a variety of techniques. If the components are sufficiently heat stable, the fibers may be sintered together. Alternatively, a number of adhesives are known, including cyanoacrylate adhesives. The space between the fibers may be completely filled by adhesive or a monomer, which is polymerized. Thermoplastic and gelling materials may also constitute the adhesive by causing a large number of fibers to be held together in a block. Even inert materials such as Teflon tubes may have their surfaces made reactive with sodium metal in a hydrocarbon solvent to etch the surfaces. Non-chemical means, such as passing an electrical current through the fibers to fuse them, may also be used.

The open ends of the capillaries may be sealed against a flat plate, by pressing a deformable material against the surface, evaporating a plastic (e.g., paralene) on the surface, or by sealing with a chemical such as a thermoplastic or thermosetting plastic material.

There are two basic options for making two-dimensional arrays from these fibers. The first is to make and evaluate ribbons, and then to form a set of ribbons into a long rectangular bar, while the second is to make the bar at the outset, and then all of the fibers together in one step. The former option appears the more advantageous since the ribbons can be evaluated individually before being formed into a complete array. Once the fiber bundle is formed, it can be sectioned using conventional microtomes to form a very large number of slices that can be attached, for example, to glass, metal, or plastic. Alternatively, one may first attach the solid phase material to the end of the bundle before sectioning the bundle. This may be performed by first coating either the end of the fiber bundle or the solid phase with, if necessary, an adhesive such as a cyanoacrylate adhesive or a pre-sectioning or post-sectioning sintering.

Dyed fibers would be visible in such arrays to confirm identifications and orientation. In addition, the fibers can be dyed in such a manner that a visible pattern is formed if the array is correctly made, and the pattern may include a name or a number.

The sliced chip present on the solid surface is then subjected to being dissolved or the matrix otherwise being removed or rendered not interfering and the agents of interest allowed to adhere directly or indirectly to the surface. To better track the individual microarrays formed, individual machine readable indicia indicating a serial number and contents of the microarray may be added thereon.

An advantage of the present system is that very large numbers of arrays may be cut, and some fraction of them used for standardization. For example, if a bar 100 cm in length were constructed, and if the bar were cut at 100-micron intervals, then 10,000 arrays would be available. If the sections were 10 microns in thickness, then the number of arrays would be 100,000.

If the individual fibers were 100 microns in diameter, there would be 100 fibers per ribbon, and 10,000 in a bar of fibers with a cross-sectional area of 1 cm square. If there were 330 per ribbon, then the total number would be 108,900, approximately the number of expressed genes postulated to be present in the human genome.

The present invention is the first array to have such a large number of different cells per unit area on a microarray without the binding agent being covalently attached to the chip. It is preferred for the present invention to have at least 100, more preferably 250, 500, 1,000, 5,000, 10,000, 20,000, 100,000 or a million or more cells per square centimeter of array. These are much higher concentrations than depositable cells formed by microfluidics in commercial microarrays.

To greatly increase the number of cells per square centimeter beyond even these high numbers, one may prepare a large fiber bundle with relatively large fibers and stretch or draw the bundle. This is typically done with deformable solids optionally with application of heat, etc. While this makes the individual fibers thinner, it does not affect their basic composition or their orientation with respect to each other and cross-section geometry. This technique has the twin advantages of allowing one to make more microarrays and making them smaller. By using a plastic embedding medium such as a low melting point wax, the result are deformable or ductile fibers which may be drawn to very thin fibers of less than 20 microns in diameter. The field of drawing thermoplastic materials is well known per se. Even if not truly drawable through a die, one can pull or extrude plastic materials between rollers to lengthen and reduce the diameter of the fibers. With optional application of gentle heat or solvent vapors, one need only pull the ends of the fiber bundle to generate the same lengthening and reducing of cross-sectional area. Fibers may be drawn to even thinner dimensions thereby permitting microarrays of in the millions to a billion or more addressable locations per square centimeter of microarray.

In the field of fiber optics, bundles of optical fibers are heated and drawn into extremely thin optical fibers while retaining their registry within the bundle. Likewise, candy canes and candy with cross-sectional designs are prepared by drawing a large block. Even glass beads used for hundreds of years were also prepared by such techniques.

When using porous particles and immobilizing the molecule of interest inside the porous particle, it may be desirable to retain a suitable fluid inside the pores and use an immiscible embedding medium. In this arrangement, the embedding medium may be incompatible with the molecule of interest or its use in a binding assay, yet still be used. For example, an aqueous solution may be used to protect proteins and a low melting point wax used to embed the porous particles.

The known photochemical processes of Fodor et al., Nature 364:555–6 (1993); Hacia et al., Molecular Psychiatry 3:483–92 (1998); and Fodor et al., Science 251:767–773 (1991) prepare short peptides and oligonucleotides covalently bound to the supporting chip. The process of amino acid or nucleotide synthesis inherently limits the practical length. Synthesis of entire proteins or genes on chips is not practical. Additionally, the secondary, tertiary and quaternary structure of the proteins may be important. By contrast, the present invention permits such.

Many different arrays may ultimately be required, and some of these, especially those developed for the identification of infectious agents, may need to be changed at frequent intervals. Further, as new disease-associated alleles are discovered, these will need to be incorporated into new arrays. To fill these requirements and allow changes and additions in arrays, it is important to have individual, stable fiber rolls available, and to have the rolls unambiguously identified. Each roll may be identified by the use of microstripes applied at short intervals along the roll. In addition, different tubes may have different colors, and non-fluorescent dyes incorporated into the gels serve as identifiers, or bar coding, may be printed on individual fibers.

Not only can the chips of the present invention be used to identify infectious agents by identifying characteristic nucleic acid sequences, they can also be used for identifying intact bacteria, mycoplasmas, yeast, nanobacteria, and viruses using arrays of immobilized specific antibodies.

This system may be used for the identification of viruses or other infectious particles isolated by microbanding tubes, WO99/46047. Thus microbes from biological samples, e.g. serum or plasma, may be concentrated, stained with a fluorescent nucleic acid stain such as TOTO-1 or YOPRO-1, and then allowed to find their matching antibodies on the array. They may then be detected by scanning for fluorescence and identified by position. It is equally a part of the present invention to immobilize microorganisms or other molecules of interest in the described chips, to use them to localize antibodies from a patient's serum, and to then discover the location of the latter using a fluorescent anti-human antibody, thus diagnosing the disease which elicited antibody production.

By using the present invention, one avoids the difficulties of individually depositing a different reagent on each cell on a solid phase or synthesizing a different compound at each cell. The former technique is limited by both the possibilities of spilling and mixing reagents and by limitations in the accuracy of measurement of small fluid volumes. Further, many proteins are not stable over a long period of time in solution. If arrays are prepared from multiple liquid reagents, these must all be assayed at intervals to ensure adequate stability. Further complicating the use of proteins in liquids is that different proteins degrade at different rates, which may cause unreproducability with microarrays not stabilized by immobilization and/or drying. The latter technique is limited by the types of different compounds that can be synthesized on a solid phase surface. Both prior art techniques are expensive and require elaborate automated equipment or tedious labor to produce each array individually. By contrast, the present invention for producing microarrays is technically simple and quick, and the batch size may be in the thousands.

Because the bundle is maintained, additional fibers or ribbons may be added to the bundle as needed before sectioning additional arrays. This allows one to detect and measure newly discovered emerging diseases, new proteins, genes or compounds without recreating a completely new bundle.

This invention may be applied in an alternative fashion in which the bundles are stored at user sites, and the arrays only sliced off as needed. This arrangement may be useful for research purposes where identical arrays are required over the long term, but only a few are required at any one time.

The invention also allows different immobilization technologies, different classes of immobilized agents of interest, different classes of analytes, and different types of detection methodologies to be employed on the same chip.

Since channels are reproducible between plates, the location of each channel or cell may be accurately determined by mechanical means. Reference markings on polished edges or other suitable locations, further identify each cell in the array. Current commercially available computer driven two-dimensional drives of sufficient accuracy are commercially available so that each cell may individually be visualized or tested, or material may be added thereto or withdrawn therefrom.

Surface treatment with a material repellant to the fluid to be eventually located inside each cell further reduces cross leakage. For example, fluorinating (Teflonizing) or silanizing agents repel water thereby generating sufficient surface tension to reduce cross leakage between cells of the microarray. Additionally, should the boarders of each cell be somewhat uneven, smeared or touching another cell, the material out of place may be burned off by application of a laser between the individual addresses of the microarray.

After sections have been cut from a bundle, they are generally bound to a solid backing to provide structural support and ease of handling. The solid backing is typically a sheet of plastic or metal although other materials may be used. The attachment maybe done by a permanent adhesive or heat fusion followed by removal of the matrix.

Individual cells in the array may be detected or visualized by scanning the entire array or portions thereof (e.g., one or a few cells) with a charged coupled device (CCD) or by illuminating one or a few channels at a time, such as by a condenser lens and objective lens. The absorbance and emission of light may thus be detected. An optical fiber bundle aligned and registering with the microarray may be used for optically detecting differences between the cells of the microarray.

Detection may be based on a large number of detectable labels including radioactive, enzyme, luminescent, optically absorbent dye, magnetic, spin-labeled, oxidizers or reducers, chemiluminescence, electrical conductance or indirect labels which interact with a detectable component interacting with the agents of interest in the microarray. The preferred detectable labeling system is based on fluorescence, usually epifluorescence. This requires that the interrogating sample be labeled with one or more fluorescent dyes. The amount of test material required is very small since it would be applied to the arrays as a thin dilute film. Hybridization of nucleic acids would be done under conditions of carefully controlled stringency.

To distinguish selected channels, one may either seal off the selected channels and/or fill them with an easily detectable substance. Different colored inks, dyes and colored materials are particularly well suited as well as detectable components similar to or opposite from the detectable component(s) being detected in other cells. Printing methods with drying inks or plastics, sublimation, solvent containing an ink or ink-jet printing may be used. The indicia so formed permits better alignment or easily detectable marking when the array is in use. This permits easy optical alignment.

Once the microarray has been used in a binding assay and the ligands are bound to the receptors, in certain instances it may be useful to provide further identification of the ligand. In certain situations, one does not know the entire structure of the ligand from the receptor that specifically binds to it. For example, if the ligand is a cell, a macromolecular complex, or a derivitized molecule with the derivitized portion acting as the ligand, etc., further analysis may be desirable. In this situation, one may elute the ligands from the microarray and collect them for further analysis. For antibody/antigen binding, a pH 2–3 environment or other conditions should strip the ligands. For nucleic acid hybridization, raising the temperature should strip the ligands. A variety of other chemical, physical and electrical techniques for breaking such bonds are known per se.

To enhance specificity to the elution process, an electrode may be placed directly over one or a subset of cells and a current passed through the microarray to release the ligands at that location. The electrode may also be part of a micropipette system to collect the released analytes, see U.S. Pat. No. 5,434,049. Preferably, one uses a porous membrane and applies a current on opposite sides of the membrane. Thin wires may be applied on, in or behind the solid surface.

The method used for analysis of the eluate may be capillary electrophoresis, mass spectrometry or a second binding assay. Convenient to mass spectrometry, the microarray itself may be introduced into a laser-desorption system incorporated into a mass spectrometry system wherein bound molecules are desorbed and analyzed.

Once the analytes have been striped from the microarray, the microarray may be reused. This reuse process has the advantage of being standardized by multiple controls over time.

The previous methodology for preparation of protein chips requires preparation, use and reuse of large numbers of proteins in solution. Proteins, nucleic acids, biological cells, other chemicals and complexes in solution are unstable and deteriorate over time. Even if frozen, repeated use may involve repeated freeze-thaw cycles that denature certain proteins as well. By contrast, immobilized proteins have been shown to be stable over long periods of time.

The following examples are included for purposes of illustrating certain aspects of the invention and should not be construed as limiting.

EXAMPLE 1

Formation and Analysis of a Microarray

The solid phase (i.e., supporting surface for chip/antibody deposition) is modified by trapping protein G (a bacterial protein capable of binding many immunoglobulins by their Fc domain) to the surface by activating the surface at predetermined sites with 0.2M N-ethyl-N'-(3-dimethylaminopropyl)carbodiimide (EDC) and 0.05M N-hydroxysuccinimide (NHS) in distilled water, applying protein G in coupling buffer (10 mM sodium acetate, pH 5.0) to the activated surfaces, and deactivating any excess of EDC and NHS with IM ethanolamine, pH 8.5.

Polyclonal antibodies directed against human serum albumin (HSA), transferrin (Tf), and haptoglobin (Hp) from commercial sources are used. Antibody containing fibers are prepared by mixing at 50° C. the antiserum solution preparation with matrix in approximately the ratios of 65% antibody containing PBS, 12% stearoxymethylsilane, 10% propylene glycol, 7% stearyl alcohol, 2% hydrogenated castor oil (castor wax), 1.5% PEG-4 castor oil, 1.5% PPG-5 ceteth-20, and 1% Ceteareth-20.

The solution for the rabbit anti-HSA is modified to contain green food coloring to distinguish it. Likewise, the anti-Tf and Hp are colored blue, the mixed anti-HSA, Tf and Hp is colored yellow and the non-antibody containing control was white (uncolored). Each melted combination is sucked into a length of one mm diameter plastic tubing of 10 cm in length attached to a 1 ml syringe and plunged in ice water. The fiber is allowed to gel into a soft solid. The rods thus obtained are laid into an aluminum channel with ImmunoBed (polymethacrylate) to form an array of 2×2 parallel rods embedded in a square cross-section bar of ImmunoBed.

After the bar gels, it is removed from the aluminum channel mold, and transverse sections are prepared by slicing thin slices perpendicular to the axis of the bar (and the filaments) and mounted on a glass slide. These sections revealed a pattern of 4 circular areas (the fibers) surrounded by clear embedding matrix by microscopy. The sliced section is placed in the predetermined sites of the modified solid phase and allowed to adhere. The solid phase is heated to 50° C. to melt the matrix and the antibodies are then allowed to interact with the protein G modified surfaces of the solid phase. After an appropriate time, the surface is blotted for bulk removal of the matrix and the remainder is removed by applying negative pressure to the solid phase surface. The solid phase is then sufficiently washed to remove matrix and unbound antibody.

In order to test specific protein binding to the surface at the addresses forming the microarray, commercially available HSA and Tf protein are labeled with fluorescein isothiocyanate (FITC) on Cellite (from Sigma). Cellite is a commercial carrier for insoluble FITC. These proteins are dissolved in about 4 ml of 0.4M sodium bicarbonate buffer (~pH 8.3) and added to the dry FITC on Cellite.

The reaction is conducted under conditions to allow for maximal conjugation. The Cellite is removed by centrifugation, and the supernatant protein and unreacted dye placed in a centrifugal protein concentrator, where the protein is washed by repeated dilution and re-concentration in buffer. The fluid is centrifuged to remove the Cellite and supernatant recentrifuged with 4 ml sodium bicarbonate buffer until clear.

The addresses are exposed to a solution of fluorescently labeled HSA. The microarray is then washed extensively in PBS, and re-examined under an epifluorescence microscope equipped with a 500 nm low pass filter and a 510 nm high pass filter for fluorescein fluorescence detection and a 35 mm camera.

EXAMPLE 2

Manufacture and use of Diagnostic Array Detecting Autoantibodies to Mitochondrial or Lysosomal Proteins.

Suspensions of whole isolated rat and mouse liver mitochondria, lysosomes, and expressed proteins are suspended or dissolved in an aqueous buffer, at 10 mg/ml concentration, and optionally fixed with glutaraldehyde (1%). 1 ml of each preparation is mixed with low temperature gelling agarose. The mixture is placed in a syringe and injected into 0.0625 inch internal diameter Teflon tubing under anaerobic conditions. The ends of the tubes are then heat sealed and stored cold until used, or are immediately extruded for use in preparing a fiber bundle. Bundles are prepared by laying 10 or more fibers in parallel, to make a single-layered array, in an elongated Teflon box. JB-4 resin without protein is then poured in, the box briefly evacuated to remove air bubbles, and the resin allowed to set. Several such flat arrays may then be stacked in parallel to make a three-dimensional groupings, and the whole grouping further vacuum impregnated to form a three-dimensional bundle. After polymerization, the bundle is cut with a glass microtome knife to give sections 5–20 microns thick, and the sections placed on glass slide. The sections are mounted on EDC/NHS (as the heterobifunctional linking agent) activated glass slides.

Microarrays are made by melting and processing as described in Example 1. In other trials, the solid phase comprises the moiety in Thust et al. U.S. Pat. No. 5,955,335. In either case, gelling matrix is inert with respect to the heterobifinctional moiety, and after melting, the immobilized biomaterials are allowed to interact with the solid phase surface. The matrix is removed as described in Example 1.

Tests for autoantibodies are done by placing 0.25 mL of a 1:10 dilution of human serum at each address and incubating the arrays at 25° C. for 20 minutes. The arrays are then rinsed in phosphate buffered saline four times, and are then immersed in a solution of goat antihuman globulin conjugated with horseradish peroxidase. After a further 20 minute incubation, the arrays are again washed four times with buffer, and then placed in a solution of 3,3', 5,5'-tetramethylbenzidine in an organic base to which is added a hydrogen peroxide solution (0.02%) in a citric acid buffer. An insoluble blue color indicates the presence of autoantibodies.

EXAMPLE 3

Protein Immobilized Microarrays

A membrane of PVDF is used as the solid surface to form a microarray. A 5% acrylamide protein containing buffer solution is prepared for HSA, haptoglobin and transferring and sucked into a 1 mm diameter plastic tube as in Example 1 and polymerized. The remainder of the sliced section preparation process of Example 1 is repeated.

After placing the sliced section on the PVDF membrane, the entire setup is placed in an electrophoresis system, submerged in buffer and the protein electrophoresed to the membrane. After removal, the sliced section is physically removed the microarray washed.

Fluorescently labeled antibody preparations (labeled as above) to each of the proteins are applied to separate microarrays and the results observed by epifluorescence microscopy.

EXAMPLE 4

Anticancer Diagnostic and Drug Screening

Suspensions of various fresh cells from a leukemia patient, several leukemia cell lines (HTB, ATCC), normal peripheral white blood cells and normal bone marrow cells in PBS with 2% sodium alginate are prepared. A commercial dialysis hollow fiber membrane is cut in half and the hollow fibers spread apart. Individual hollow fibers are added 2 ml tubes of each cell suspension. The fluid is draw through each fiber by aspiration. The ends are heat sealed and the apparatus submerged in 1% calcium chloride in saline solution for ten minutes to permit diffusion of calcium ions. The end block of the hollow fiber dialysis apparatus is sectioned transversely by a microtome at 10 microns thick. Thin section slices are placed on a porous nylon membrane. A piece of filter paper is saturated with 5 g/l sodium EDTA solution, placed in a humidified chamber and the nylon membrane placed on top and incubated for one hour. The nylon membrane is removed, washed and the section slices removed to form a microarray.

The cells attached to the nylon are alkaline-lysed and protease K-digested by standard procedures for in situ hybridization. The microarrays are heat denatured and a digoxigeninlabeled DNA probe for the following genes: N-myc, C-myc, K-ras, p53, HER-2/neu and a candidate DNA probe for diagnostic purposes are applied thereto. Texas Red-labeled anti-digoxigenin antibody is added and the pattern and amount of binding are determined by fluorescent microscopy.

It will be understood that various modifications may be made to the embodiments disclosed herein. Therefore, the above description should not be construed as limiting, but merely as exemplifications of preferred embodiments.

Those skilled in the art will envision other modifications within the scope and spirit of the claims appended hereto.

All patents and references cited herein are explicitly incorporated by reference in their entirety.

REFERENCES

Books

Hermanson, Greg T. Bioconjugate Techniques. Academic Press, New York. 1995, 785 pp.

Hermanson, G. T., Mallia, A. K. & Smith, P. K. Immobilized Affinity Ligand Techniques. Academic Press, 1992, 454 pp Periodicals Ogura, M., Agata, Y., Watanabe, K., McCormick, R. M. Hamaguchi, Y., Aso, Y., and Mitsuhashi, M. RNA chips: Quality assessment of RNA by microchannel linear gel electrophoresis in injection-molded plastic chips. Clin. Chem. 44: 2249–55, 1998.

Johnston, M., Gene chips: Array of hope for understanding gene regulation. Cur. Biol. 8: R171–4, 1998.

Jordan, B. R., Large-scale expression mesurement by hybridization methods: from highdensity membranes to "DNA chips". J. Biochem. (Tokyo) 124: 251–8, 1998.

Pevzner, P. A., Lysov, Yu. P., Khrapko, K. R., Belyavsky, A. V., Florentiev, V. L. and Mirzabekov, A. D. J. Biol. Struct. Dyn. 9: 399–410, 1991.

Hacia, J. G., Brody, L. C., Collins, F. S. Applications of DNA chips for genomic analysis. Mol. Psychiatry 3: 483–92, 1998.

Ramsay, G., DNA chips: State of the art. Nat. Biotechnol. 16: 40–4. 1998

Kozal, M., Chee, M., Shah, N. Yang, R., Gingeras, T. Development of DNA chips for the rapid sequence analysis and the development of drug resistant mutations for the HIV protease and reverse transcriptase genes. Natl. Conf. Hum. Retroviruses Relat. Infect. ($2^{nd}$) 1995:93.

Fodor, S. P., Rava, R. P., Huang, X. C., Pease, A. C., Holmes, C. P., Adams, C. L. Multiplexed biochemical assays with biological chips. Nature 364: 555–6, 1993.

Fodor, S. P. A., Read, L. J., Pirrung, M. C., Stryer, L., Lu, A. M., and Solas, D. Light-directed spatially addressable parallel chemical synthesis. Science 251: 767–773, 1991.

Cheng, J., Shoffner, M. A., Hvichia, G. E., Kricka, L. J., and Wilding, P. Chip PCR II. Investigation of different PCR amplification systems in microfabricated silicon-glass chips. Nucleic Acids Research 24: 380–5, 1996.

Woolley, A. T., and Mathies, R. A. Ultra-high-speed DNA fragment separations using microfabricated capillary array electrophoresis chips. PNAS USA 91: 11348–52, 1994

Southern, E. M., DNA chips: Analysing sequence by hybridization to oligonucleotides on a large scale. Trends in Genetics. 12: 110–5, 1996.

Birnbaum, S., Uden, C., Magnusson, G. M., and Nilsson, S. Latex-based thin layer immunoaffinity chromatography of quantitation of protein analytes. Analytical Biochemistry. 206: 168–171, 1992.

Bellara, S. R., Cui, Z., MacDonald, S. L., and Pepper, D. S. Virus removal from bioproducts using ultafiltration membranes modified with latex particle pretreatement. Bioseparations 7: 79–88, 1998.

Van Oss, C. J., and Singer, J. M. The binding of immune globulins and other proteins by polystryene latex particles. J. Reticuloendothelial Society 3: 29040, 1966.

Arlinghaus, H. F., Kwoka, M. N., and K. Bruce Jacoson Analysis of biosensor chips for identification of nucleic acids. Anal. Chem. 69: 3747–3753, 1997.

Wang, J., Cai, X., Rivas, G., Shiraishi, H., and Dontha, N. Nucleic-acid immobilization recognition and detection at chronopotentiometric DNA chips. Biosensors & Bioelectronics 12: 587–599, 1997.

Livache, T., Bazin, H., Caillat, P., and Roget, A. Electroconducting polymers for the construction of DNA or peptide arrays on silicon chips. Biosensors and Bioelectronics 13: 629–634, 1998.

Syvanen, A–C. From gels to chips: "Minisequencing" primer extension for analysis of point mutations and single nucleotide polymorphisms. Human Mutation 13: 1–10, 1999.

Shevalier, A., Mikhailov, M., and Nikolaeva, I. New fast low-cost method of HIV dignostics based on carbon-conjugated antigens. Abstr. PB0420 Itent International Conferences on AIDS. Abstr. Book Volume 1. Internationatl Conference on STD. Yokohama Japan, Aug. 7–12, 1994.

Inomata, Y., Wada, T., Handa, H., Fujimoto, K., and Kawaguchi, Preparation of DNA-carrying affinity latex and purification of trascription factors with the latex. J. Biomaterial Sci., Polymer Edn. 5: 293–301, 1994.

Balhorn, R., Allen, M., Tensch, B., Marzrimaz, J. A., Balooch, M., Siekhaus, W., Imaging of DNA molecules deposited on graphite, in "DOE/NIH Human Genome Contractors.Grantee Workshop", Santa Fe, 34 (1989).

Sundarababu, G., Gao, H, and Sigrist, H. Photochemical linkage of antibodies to silicon chips. Photochemistry and Photobiology 61: 540–544, 1995.

Regnier, F. E., He, B., Lin, S., and Busse, J. Chromatography and electrophoresis on chips: Critical elements of future integrated, microfluidic analytical systems for life scinece. Trends in Biotechnology 17: 101–106. 1999

Patents

U.S. Pat. No. 5,843,767 Microfabricated, flow-through porous apparatus for discrete detection of binding reactions.

U.S. Pat. No. 4,289,623 Hollow fiber dialysis

U.S. Pat. No. 3,976,576 Dialyzer cartridge—Also, use of dialyzer cartridge by filling hollow fibers and embed protein in fibers as they are formed before the cartridges are cut.

U.S. Pat. No. 5,817,470 Biomaterial immobilization on an $Si_3N_4$ surface containing SI-$NH_2$ groups with a heterobifunctional cross-linking agent.

U.S. Pat. No. 5,716,854 Immobilization of antigens to solid support by the mussel adhesive polyphenolic protein and the method of use therein.

U.S. Pat. No. 5,955,335 Test plates for agglutination test and production process thereof.

U.S. Pat. No. 5,736,099 Solid phase binding assay.

U.S. Pat. No. 5,162,582 N-(2-methoxyethyl)-N-isoproprylacrylamide, hydrophillic-hydrophobic thermally reversible macromolecular compound, method of production thereof, and thermally reversible macromolecular composition.

U.S. Pat. No. 4,822,848 Hydrophilic-hydrophobic thermally reversible type polymer and method for producing thereof.

What is claimed is:

1. A method of dry dispensing a binding molecule in a defined area on a surface comprising:

(1) placing a solid in said area on said surface without the use of a liquid vehicle, wherein said solid comprises a matrix and said binding molecule, wherein said binding molecule is entrapped in said matrix, and wherein each of a plurality of defined areas comprises a different binding molecule;

(2) degrading said matrix of step (1);

(3) substantially removing degraded matrix from said surface to allow said binding molecule to be deposited in said defined area; and (4) retaining said binding molecule on said surface, wherein said retaining step uniformly adheres said binding molecule to said defined area on said surface.

2. The method of claim 1, wherein said solid is formed from a transversely sliced section of a fiber.

3. The method of claim 2, wherein at least 100 fibers are bundled in a fixed alignment with respect to each other.

4. The method of claim 1, wherein said matrix is selected from the group consisting of super-cooled liquid, crystal, plastic, and colloid suspension.

5. The method of claim 1, wherein said entrapped binding molecule is a biological macromolecule.

6. The method of claim 5, wherein said macromolecules are selected from the group consisting of proteins, carbohydrates, nucleic acids, and lipids.

7. The method of claim 1, wherein said solid is positioned on at least one porous membrane which abuts said surface or is said surface, before degrading said matrix.

8. The method of claim 7, wherein the matrix is removed by passage through the porous membrane.

* * * * *